United States Patent
Trama et al.

(10) Patent No.: US 9,145,593 B2
(45) Date of Patent: Sep. 29, 2015

(54) **OLIGONUCLEOTIDES USEFUL IN METHODS FOR DETECTING AND CHARACTERIZING *ASPERGILLUS FUMIGATUS***

(71) Applicants: Jason Trama, Burlington, NJ (US); Martin E Adelson, East Windsor, NJ (US); Eli Mordechai, Robbinsville, NJ (US)

(72) Inventors: Jason Trama, Burlington, NJ (US); Martin E Adelson, East Windsor, NJ (US); Eli Mordechai, Robbinsville, NJ (US)

(73) Assignee: Medical Diagnostic Laboratories, LLC, Hamilton, NJ (US)

( * ) Notice: Subject to any disclaimer, the term of this patent is extended or adjusted under 35 U.S.C. 154(b) by 0 days.

(21) Appl. No.: 13/461,122

(22) Filed: Sep. 17, 2012

(65) Prior Publication Data
US 2013/0230848 A1 Sep. 5, 2013

Related U.S. Application Data

(62) Division of application No. 11/299,362, filed on Dec. 9, 2005, now abandoned.

(60) Provisional application No. 60/636,133, filed on Dec. 15, 2004.

(51) Int. Cl.
*C12Q 1/68* (2006.01)

(52) U.S. Cl.
CPC .............. *C12Q 1/6895* (2013.01); *C12Q 1/689* (2013.01); *C12Q 2561/113* (2013.01); *C12Q 2565/301* (2013.01); *C12Q 2600/156* (2013.01)

(58) Field of Classification Search
None
See application file for complete search history.

(56) References Cited

PUBLICATIONS

Diaz-Guerra et al. Antimicrobial Agents and Chemotherapy 47: 1120-1124 (2003).*
Ronaghi, M. Genome Research 11: 3-11 (2001).*
Erlich et al. Science 252: 1643-1651 (1991).*
Mothershed et al. Journal of Clinical Microbiology 40: 4713-4719 (2002).*
Pryce et al. Diagnostic Microbiology and Infectious Disease 47: 487-496 (2003).*
Alderborn et al. Genome Research 10: 1249-1258 (2000).*
GenBank Accession No. AF338659 (Jul. 2001).*

* cited by examiner

*Primary Examiner* — Angela M Bertagna
(74) *Attorney, Agent, or Firm* — Siu K. Lo

(57) ABSTRACT

Methods for using oligonucleotides in the detection of *Aspergillus fumigatus* are disclosed. The oligonucleotides of the invention have nucleotide sequences derived from the gene encoding the cytochrome P450 14 alpha-sterol demethylase (the cyp51A protein) of *Aspergillus fumigatus*. The oligonucleotides include primers capable of producing amplicons specific to cyp51A in polymerase chain reactions using nucleic acids isolated from *Aspergillus fumigatus* as templates. The oligonucleotides also include probes capable of detecting these cyp51A-specific amplicons. The oligonucleotides of the invention also include primers for nucleotide sequencing reactions to determine whether an isolate of *Aspergillus fumigatus* is more tolerant than wild-type *Aspergillus fumigatus* to a triazole.

3 Claims, 2 Drawing Sheets

TAC GGG ATT GAT CCC TAC AAG TTC TT

SEQ ID NO: 50

TAC GGG ATT GAT CCC

SEQ ID NO: 51

US 9,145,593 B2

OLIGONUCLEOTIDES USEFUL IN METHODS FOR DETECTING AND CHARACTERIZING *ASPERGILLUS FUMIGATUS*

CROSS-REFERENCE TO RELATED APPLICATIONS

This application is a divisional of application Ser. No. 11/299,362, filed Dec. 9, 2005, now abandoned, which claims the benefit under 35 U.S.C. 119(e) of U.S. Provisional Application No. 60/636,133 filed Dec. 15, 2004, the entire content of which is hereby incorporated by reference in their entirety.

FIELD OF THE INVENTION

The present invention is broadly concerned with oligonucleotides useful in methods for detecting and characterizing *Aspergillus fumigatus*. More particularly, the present invention relates to oligonucleotides having nucleotide sequences derived from the gene encoding the cytochrome P450 14 alpha-sterol demethylase (i.e., the Cyp51A protein) of *Aspergillus fumigatus*, wherein these oligonucleotides are useful as forward and reverse primers for a polymerase chain reaction using nucleic acids from a biological sample as a template, as probes for detecting any resultant cyp51A-specific amplicon indicating the presence of *Aspergillus fumigatus* in the sample, and as nucleotide sequencing primers for detecting cyp51A mutations responsible for increased tolerance or resistance of *Aspergillus fumigatus*, relative to wild-type *Aspergillus fumigatus*, to at least on triazole.

BACKGROUND OF THE INVENTION

*Aspergillus fumigatus* is the causative agent for medical conditions including invasive aspergillosis, which is a major cause of morbidity and mortality in immunocompromised patients. The survival of such patients depends on early diagnosis and prompt initiation of effective antifungal treatment (see Latge, 1999, *Aspergillus fumigatus* and spergillosis. Clinical Microbiology Reviews 12:310-350; and Man et al., 2002, Aspergillosis. Pathogenesis, clinical manifestations, and therapy. Infectious Disease Clinics of North America 16:875-894). Azole-based compounds (e.g., triazoles) are the most commonly used antifungal drugs. The target for these compounds is the Cyp51A protein. This protein is involved in the synthesis of ergosterol, which is a bulk sterol component of fungal cell membranes (see Vanden Bossche, 1985, Biochemical targets for antifungal azole derivatives: hypothesis on the mode of action. Current Topics in Medical Mycology 1:313-351).

Unfortunately, conventional laboratory tests for the presence of *Aspergillus fumigatus*, such as culture and galactomannan detection, lack sensitivity, and are rarely conclusive, resulting in true positive results only at advanced stages of infection or necessitating invasive procedures for formal microbiological evaluation (see Denning, 1998, Invasive aspergillosis. Clinical Infectious Diseases 26:781-803; and Latge, 1999, *Aspergillus fumigatus* and aspergillosis. Clinical Microbiology Reviews 12:310-350). Furthermore, the emergence of clinical resistance to azole-based drugs impedes successful treatment of infection by *Aspergillus fumigatus* (see Denning et al., 1997, Itraconazole resistance in *Aspergillus fumigatus*. Antimicrobial Agents and Chemotherapy 41:1364-1368; Mar et al., 2002, Aspergillosis, Pathogenesis, clinical manifestations, and therapy. Infectious Disease Clinics of North America 16:875-894; and Steinbach et al., 2003, Review of newer antifungal and immunomodulatory strategies for invasive aspergillosis. Clinical Infectious Diseases 37 Supplement 3:S157-S187).

For example, isolates of *Aspergillus fumigatus* exhibiting increased tolerance to triazoles, relative to wild-type *Aspergillus fumigatus*, have been identified. Each of these isolates was found to have a mutation in cyp51A responsible for an amino acid substitution at position 54, 138, 220, or 448 of the Cyp51A protein, wherein each of these amino acid substitutions gave rise to the reduced triazole susceptibility. (see Mann et al., 2003, Mutations in *Aspergillus fumigatus* resulting in reduced susceptibility to posaconazole appear to be restricted to a single amino acid in the cytochrome P450 14 alpha-demethylase. Antimicrobial Agents and Chemotherapy 47:577-581; Nascimento et al., 2003, Multiple resistance mechanisms among *Aspergillus fumigatus* mutants with high-level resistance to itraconazole. Antimicrobial Agents and Chemotherapy 47:1719-1726; Diaz-Guerra et al., 2003, A point mutation in the 14 alpha-sterol demethylase gene cyp51A contributes to itraconazole resistance in *Aspergillus fumigatus*. Antimicrobial Agents and Chemotherapy 47:1120-1124; Xiao et al., 2004, Three-dimensional models of wild-type and mutated forms of cytochrome P450 14 alpha-sterol demethylases from *Aspergillus fumigatus* and *Candida albicans* provide insights into posaconazole binding. Antimicrobial Agents and Chemotherapy 48:568-574; and Mellado et al., 2004, Substitutions at methionine 220 in the 14 alpha-sterol demethylase (Cyp51A) of *Aspergillus fumigatus* are responsible for resistance in vitro to azole antifungal drugs. Antimicrobial Agents and Chemotherapy 48:2747-2750).

Thus, there exists a critical need to develop techniques to facilitate the early and reliable diagnosis of invasive aspergillosis by detecting the causative agent *Aspergillus fumigatus* in an infected patient, and to ascertain whether treating this patient with a triazole would be effective by determining whether the infecting *Aspergillus fumigatus* encodes a Cyp51A protein having one or more of the above-noted amino acid substitutions.

SUMMARY OF THE INVENTION

General Overview of the Present Invention

The aforementioned drawbacks in the detection of *Aspergillus fumigatus* and in the treatment of infection by *Aspergillus fumigatus* with a triazole are avoided by the present invention. Specifically, this invention is directed to particular oligonucleotides and to combinations of these oligonucleotides, wherein the combinations are useful in a first method for determining whether a sample contains *Aspergillus fumigatus*, and second, third, fourth, and fifth methods for determining whether a particular isolate of *Aspergillus fumigatus* is more tolerant to a triazole (e.g., itraconazole, posaconazole, ravuconazole, or voriconazole) than wild-type *Aspergillus fumigatus*.

More specifically, the oligonucleotides of the present invention include forward primers and reverse primers for generating amplicons specific to nucleic acids encoding Cyp51A proteins of *Aspergillus fumigatus*, probes for detecting these amplicons, and nucleotide sequencing primers for detecting mutations responsible for amino acid substitutions at positions 54, 138, 220, and 448 of the Cyp51A protein of wild-type *Aspergillus fumigatus*, wherein these mutations give rise to increased tolerance or resistance of *Aspergillus fumigatus* to at least one triazole. The second, third, fourth, and fifth methods of the present invention are respectively directed to detection of the amino acid substitutions at positions 54, 138, 220, and 448 of the Cyp51A protein.

An isolate of *Aspergillus fumigatus* is more tolerant to a triazole than wild-type *Aspergillus fumigatus* if (a) amino acid 54 of SEQ ID NO:2 is not Gly and is, e.g., Arg, Glu, Lys, Trp, or Val, (b) amino acid 138 of SEQ ID NO:3 is not Gly and is, e.g., Arg, (c) amino acid 220 of SEQ ID NO:4 is not Met and is, e.g., Val, Lys, or Thr, and (d) amino acid 448 of SEQ ID NO:5 is not Gly, and is, e.g., Ser.

THE SEQUENCE LISTING OF THE PRESENT INVENTION

SEQ ID NO:1 is the amino acid sequence of the Cyp51A protein of wild-type *Aspergillus fumigatus*, while SEQ ID NO:6 is a sense-strand nucleotide sequence encoding this Cyp51A protein and SEQ ID NO:7 is the reverse complement of the nucleotide sequence of SEQ ID NO:6.

SEQ ID NO:2 is the amino acid sequence of a Cyp51A protein of *Aspergillus fumigatus* in which amino acid 54 is Xaa, wherein Xaa is any naturally occurring amino acid, while SEQ ID NO:8 is a sense-strand nucleotide sequence encoding this Cyp51A protein and SEQ ID NO:9 is the reverse complement of the nucleotide sequence of SEQ ID NO:8.

SEQ ID NO:3 is the amino acid sequence of a Cyp51A protein of *Aspergillus fumigatus* in which amino acid 138 is Xaa, while SEQ ID NO:10 is a sense-strand nucleotide sequence encoding this Cyp51A protein and SEQ ID NO:11 is the reverse complement of the nucleotide sequence of SEQ ID NO:10.

SEQ ID NO:4 is the amino acid sequence of a Cyp51A protein of *Aspergillus fumigatus* in which amino acid 220 is Xaa, while SEQ ID NO:12 is a sense-strand nucleotide sequence encoding this Cyp51A protein and SEQ ID NO:13 is the reverse complement of the nucleotide sequence of SEQ ID NO:12.

SEQ ID NO:5 is the amino acid sequence of a Cyp51A protein of *Aspergillus fumigatus* in which amino acid 448 is Xaa, while SEQ ID NO:14 is a sense-strand nucleotide sequence encoding this Cyp51A protein and SEQ ID NO:15 is the reverse complement of the nucleotide sequence of SEQ ID NO:14.

Each of SEQ ID NO:16 through SEQ ID NO:49 is the nucleotide sequence of an exemplary forward primer, reverse primer, probe, or nucleotide sequencing primer of the present invention.

The Oligonucleotides of the Present Invention

The present invention includes an isolated oligonucleotide capable of hybridizing, under highly stringent hybridization conditions (see below) to at least a portion of a segment of a polynucleotide, wherein the segment consists of (a) nucleotides 720 through 743, nucleotides 515 through 537, nucleotides 662 through 686, nucleotides 903 through 923, nucleotides 838 through 854, nucleotides 846 through 877, nucleotides 1212 through 1235, nucleotides 1107 through 1129, nucleotides 1085 through 1099, nucleotides 1070 through 1095, nucleotides 1784 through 1804, nucleotides 1769 through 1783, or nucleotides 1754 through 1775 of SEQ ID NO:6, or (b) nucleotides 1551 through 1574, nucleotides 1538 through 1559, nucleotides 1363 through 1387, nucleotides 1304 through 1327, nucleotides 1257 through 1277, nucleotides 1216 through 1235, nucleotides 1172 through 1203, nucleotides 1062 through 1084, nucleotides 983 through 1002, nucleotides 972 through 989, nucleotides 954 through 979, nucleotides 352 through 374, nucleotides 288 through 304, or nucleotides 274 through 295 of SEQ ID NO:7.

Highly stringent hybridization conditions include the following conditions: 6×SSC and 65° C.; hybridization conditions described in Ausubel et al., 2002, Short Protocols in Molecular Biology, $5^{th}$ edition, Volumes 1 and 2, John Wiley & Sons, Inc., Hoboken, N.J., the entire contents of which are hereby incorporated by reference; and hybridization conditions described in Ausubel et al., 1997, Short Protocols in Molecular Biology, $3^{rd}$ edition, John Wiley & Sons, Inc., New York, N.Y., the entire contents of which are hereby incorporated by reference.

Additionally, the present invention includes an isolated oligonucleotide, wherein, based on the Clustal V or W alignment method using the default parameters (see below), the oligonucleotide is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide, wherein the segment consists of (a) nucleotides 720 through 743, nucleotides 515 through 537, nucleotides 662 through 686, nucleotides 903 through 923, nucleotides 838 through 854, nucleotides 846 through 877, nucleotides 1212 through 1235, nucleotides 1107 through 1129, nucleotides 1085 through 1099, nucleotides 1070 through 1095, nucleotides 1784 through 1804, nucleotides 1769 through 1783, or nucleotides 1754 through 1775 of SEQ ID NO:6, or (b) nucleotides 1551 through 1574, nucleotides 1538 through 1559, nucleotides 1363 through 1387, nucleotides 1304 through 1327, nucleotides 1257 through 1277, nucleotides 1216 through 1235, nucleotides 1172 through 1203, nucleotides 1062 through 1084, nucleotides 983 through 1002, nucleotides 972 through 989, nucleotides 954 through 979, nucleotides 352 through 374, nucleotides 288 through 304, or nucleotides 274 through 295 of SEQ ID NO:7.

Pairwise nucleotide sequence alignments and determination of percent identities are performed using the default parameters of the Clustal V algorithm or the Clustal W algorithm, wherein both algorithms are incorporated into the Power Macintosh MegAlign 6.1 program (DNASTAR, Madison, Wis.). The default parameters for pairwise alignments using the Clustal V algorithm are as follows: Ktuple=1, gap penalty=3, window=5, and diagonals=5. The default parameters for pairwise alignments using the Clustal W algorithm are as follows: gap penalty=10.00 and gap length=0.10. The Clustal V algorithm is described in Higgins et al., 1989, Fast and sensitive multiple sequence alignments on a microcomputer. Computer Applications in the Biosciences 5:151-153. The Clustal W algorithm is described in Thompson et al., 1994, CLUSTAL W: improving the sensitivity of progressive multiple sequence alignment through sequence weighting, position specific gap penalties and weight matrix choice. Nucleic Acids Research 22:4673-80.

In preferred embodiments, each of the oligonucleotides is from 8 to 50 nucleotides long, from 12 to 24 nucleotides long, from 10 to 30 nucleotides long, from 15 to 25 nucleotides long, from 15 to 50 nucleotides long, or from 25 to 35 nucleotides long.

Preferably, each of the oligonucleotides comprises the nucleotide sequence of SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, or SEQ ID NO:49.

More preferably, each of the oligonucleotides consists of the nucleotide sequence of SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, or SEQ ID NO:49.

Advantageously, nucleotides 12, 13, and 14 of SEQ ID NO:41 are a, t, and g, respectively, nucleotides 13, 14, and 15 of SEQ ID NO:42 are c, a, and t, respectively, nucleotides 12, 13, and 14 of SEQ ID NO:48 are g, g, and t, respectively, and nucleotides 9, 10, and 11 of SEQ ID NO:49 are a, c, and c, respectively.

Oligonucleotide Combinations of the Present Invention

The present invention also is drawn to a composition (e.g., a reaction mixture or a kit) containing a forward primer and a reverse primer. In a preferred embodiment of the composition, the forward primer is capable of hybridizing, under highly stringent hybridization conditions, to at least a portion of a segment of a polynucleotide, wherein the segment consists of nucleotides 1551 through 1574, nucleotides 1304 through 1327, nucleotides 1257 through 1277, nucleotides 1062 through 1084, nucleotides 983 through 1002, or nucleotides 352 through 374 of SEQ ID NO:7, and the reverse primer is capable of hybridizing, under highly stringent hybridization conditions, to at least a portion of a segment of a polynucleotide, wherein the segment consists of nucleotides 720 through 743, nucleotides 903 through 923, nucleotides 1212 through 1235, nucleotides 1107 through 1129, or nucleotides 1784 through 1804 of SEQ ID NO:6.

In an additional preferred embodiment of the composition, the forward primer is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, wherein the segment consists of nucleotides 1551 through 1574, nucleotides 1304 through 1327, nucleotides 1257 through 1277, nucleotides 1062 through 1084, nucleotides 983 through 1002, or nucleotides 352 through 374 of SEQ ID NO:7, and the reverse primer is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, wherein the segment consists of nucleotides 720 through 743, nucleotides 903 through 923, nucleotides 1212 through 1235, nucleotides 1107 through 1129, or nucleotides 1784 through 1804 of SEQ ID NO:6.

Preferably, the combination comprises a first oligonucleotide probe or a second oligonucleotide probe, wherein the first oligonucleotide probe is capable of hybridizing, under highly stringent hybridization conditions, to at least a portion of a segment of a polynucleotide, wherein the segment consists of nucleotides 1363 through 1387 of SEQ ID NO:7, nucleotides 1172 through 1203 of SEQ ID NO:7, nucleotides 954 through 979 of SEQ ID NO:13, or nucleotides 274 through 295 of SEQ ID NO:15, and wherein the second oligonucleotide probe is capable of hybridizing, under highly stringent hybridization conditions, to at least a portion of a segment of a polynucleotide, wherein the segment consists of nucleotides 662 through 686 of SEQ ID NO:6, nucleotides 846 through 877 of SEQ ID NO:6, nucleotides 1070 through 1095 of SEQ ID NO:12, or nucleotides 1754 through 1775 of SEQ ID NO:14.

Advantageously, the first oligonucleotide probe is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, wherein the segment consists of nucleotides 1363 through 1387 of SEQ ID NO:7, nucleotides 1172 through 1203 of SEQ ID NO:7, nucleotides 954 through 979 of SEQ ID NO:13, or nucleotides 274 through 295 of SEQ ID NO:15, and the second oligonucleotide probe is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, wherein the segment consists of nucleotides 662 through 686 of SEQ ID NO:6, nucleotides 846 through 877 of SEQ ID NO:6, nucleotides 1070 through 1095 of SEQ ID NO:12, or nucleotides 1754 through 1775 of SEQ ID NO:14.

More preferably, the combination comprises a first sequencing primer or a second sequencing primer, wherein the first sequencing primer is capable of hybridizing, under highly stringent hybridization conditions, to at least a portion of a segment of a polynucleotide, wherein the segment consists of nucleotides 1538 through 1559, nucleotides 1216 through 1235, nucleotides 972 through 989, or nucleotides 288 through 304 of SEQ ID NO:7, and wherein the second sequencing primer is capable of hybridizing, under highly stringent hybridization conditions, to at least a portion of a segment of a polynucleotide, wherein the segment consists of nucleotides 515 through 537, nucleotides 838 through 854, nucleotides 1085 through 1099, or nucleotides 1769 through 1783 of SEQ ID NO:6.

Advantageously, the first sequencing primer is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, wherein the segment consists of nucleotides 1538 through 1559, nucleotides 1216 through 1235, nucleotides 972 through 989, or nucleotides 288 through 304 of SEQ ID NO:7, and the second sequencing primer is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, wherein the segment consists of nucleotides 515 through 537, nucleotides 838 through 854, nucleotides 1085 through 1099, or nucleotides 1769 through 1783 of SEQ ID NO:6.

Most preferably, the composition contains a forward primer, a reverse primer, a first or second oligonucleotide probe, and a first or second sequencing primer, wherein each of these oligonucleotides is described above.

The First Method of the Present Invention

The first method of the present invention, which is a method for determining whether a sample contains *Aspergillus fumigatus*, comprises the following steps:

(a) providing a vessel containing a composition, wherein the composition contains a forward primer, a reverse primer, and a nucleic acid from the sample, wherein the composition is capable of amplifying, by a polymerase chain reaction, a segment of the nucleic acid to produce an amplicon, wherein production of the amplicon is primed by the forward primer and the reverse primer, wherein the amplicon encodes at least a portion of a Cyp51A protein, (b) incubating the vessel under conditions allowing production of the amplicon if the sample contains *Aspergillus fumigatus*, wherein, during production of the amplicon, the forward primer is capable of hybridizing to at least a portion of a segment of the antisense strand of the amplicon, and the reverse primer is capable of hybridizing to at least a portion of a segment of the sense strand of the amplicon, wherein the segment of the antisense strand of the amplicon consists of nucleotides 1551 through 1574, nucleotides 1304 through 1327, nucleotides 1257 through 1277, nucleotides 1062 through 1084, nucleotides 983 through 1002, or nucleotides 352 through 374 of SEQ ID NO:7, wherein the segment of the sense strand of the amplicon consists of nucleotides 720 through 743, nucleotides 903 through 923, nucleotides 1212 through 1235, nucleotides 1107 through 1129, or nucleotides 1784 through 1804 of SEQ ID NO:6, and (c) determining that the sample contains *Aspergillus fumigatus* if the amplicon is detected, or determining that the sample does not contain *Aspergillus fumigatus* if the amplicon is not detected.

Each of the forward primer and the reverse primer is preferably from 8 to 50 nucleotides long, more preferably from 12 to 24 nucleotides long.

Preferably, the forward primer is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, wherein the segment consists of nucleotides 1551 through 1574, nucleotides 1304 through 1327, nucleotides 1257 through 1277, nucleotides 1062 through 1084, nucleotides 983 through 1002, or nucleotides 352 through 374 of SEQ ID NO:7. More preferably, the forward primer comprises the nucleotide sequence of SEQ ID NO:16, SEQ ID NO:28, SEQ ID NO:29, SEQ ID NO:35, SEQ ID NO:36, or SEQ ID NO:43. Most preferably, the forward primer consists of the nucleotide sequence of SEQ ID NO:16, SEQ ID NO:28, SEQ ID NO:29, SEQ ID NO:35, SEQ ID NO:36, or SEQ ID NO:43.

Preferably, the reverse primer is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, wherein the segment consists of nucleotides 720 through 743, nucleotides 903 through 923, nucleotides 1212 through 1235, nucleotides 1107 through 1129, or nucleotides 1784 through 1804 of SEQ ID NO:6. More preferably, the reverse primer comprises the nucleotide sequence of SEQ ID NO:17, SEQ ID NO:30, SEQ ID NO:37, SEQ ID NO:38, SEQ ID NO:44, or SEQ ID NO:45. Most preferably, the reverse primer consists of the nucleotide sequence of SEQ ID NO:17, SEQ ID NO:30, SEQ ID NO:37, SEQ ID NO:38, SEQ ID NO:44, or SEQ ID NO:45.

In preferred embodiments, in (b), the vessel contains a first oligonucleotide probe or a second oligonucleotide probe capable of detecting the amplicon if the amplicon is produced in (b). Each of the first oligonucleotide probe and the second oligonucleotide probe is preferably from 15 to 50 nucleotides long, more preferably from 25 to 35 nucleotides long.

In more preferred embodiments, the first oligonucleotide probe is capable of hybridizing to at least a portion of a segment of the antisense strand of the amplicon, wherein the segment consists of nucleotides 1363 through 1387 of SEQ ID NO:7, nucleotides 1172 through 1203 of SEQ ID NO:7, nucleotides 954 through 979 of SEQ ID NO:13, or nucleotides 274 through 295 of SEQ ID NO:15. Preferably, the first oligonucleotide probe is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, wherein the segment consists of nucleotides 1363 through 1387 of SEQ ID NO:7, nucleotides 1172 through 1203 of SEQ ID NO:7, nucleotides 954 through 979 of SEQ ID NO:13, or nucleotides 274 through 295 of SEQ ID NO:15. More preferably, the first oligonucleotide probe comprises the nucleotide sequence of SEQ ID NO:26, SEQ ID NO:33, SEQ ID NO:41, or SEQ ID NO:48. Most preferably, the first oligonucleotide probe consists of the nucleotide sequence of SEQ ID NO:26, SEQ ID NO:33, SEQ ID NO:41, or SEQ ID NO:48. Advantageously, nucleotides 12, 13, and 14 of SEQ ID NO:41 are a, t, and g, respectively, and nucleotides 12, 13, and 14 of SEQ ID NO:48 are g, g, and t, respectively.

Additionally, in more preferred embodiments, the second oligonucleotide probe is capable of hybridizing to at least a portion of a segment of the sense strand of the amplicon, wherein the segment consists of nucleotides 662 through 686 of SEQ ID NO:6, nucleotides 846 through 877 of SEQ ID NO:6, nucleotides 1070 through 1095 of SEQ ID NO:12, or nucleotides 1754 through 1775 of SEQ ID NO:14. Preferably, the second oligonucleotide probe is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, wherein the segment consists of nucleotides 662 through 686 of SEQ ID NO:6, nucleotides 846 through 877 of SEQ ID NO:6, nucleotides 1070 through 1095 of SEQ ID NO:12, or nucleotides 1754 through 1775 of SEQ ID NO:14. More preferably, the second oligonucleotide probe comprises the nucleotide sequence of SEQ ID NO:27, SEQ ID NO:34, SEQ ID NO:42, or SEQ ID NO:49. Most preferably, the second oligonucleotide probe consists of the nucleotide sequence of SEQ ID NO:27, SEQ ID NO:34, SEQ ID NO:42, or SEQ ID NO:49. Advantageously, nucleotides 13, 14, and 15 of SEQ ID NO:42 are c, a, and t, respectively, and nucleotides 9, 10, and 11 of SEQ ID NO:49 are a, c, and c, respectively.

The Second Method of the Present Invention

The second method of the present invention, which is a method for determining whether an isolate of *Aspergillus fumigatus* is more tolerant to a triazole than wild-type *Aspergillus fumigatus*, comprises the following steps:

(a) providing a vessel containing a composition, wherein the composition contains a forward primer, a reverse primer, and a nucleic acid isolated from the isolate, wherein the composition is capable of amplifying, by a polymerase chain reaction, a segment of the nucleic acid to produce an amplicon, wherein production of the amplicon is primed by the forward primer and the reverse primer, wherein the amplicon encodes at least a portion of a Cyp51A protein, wherein the sense strand of the amplicon contains at least the first nucleotide of the codon corresponding to the codon encoding amino acid 54 of SEQ ID NO:2, wherein the codon encoding amino acid 54 of SEQ ID NO:2 consists of nucleotides 512, 513, and 514 of SEQ ID NO:8, wherein the reverse complement of the codon encoding amino acid 54 of SEQ ID NO:2 consists of nucleotides 1535, 1536, and 1537 of SEQ ID NO:9, (b) incubating the vessel under conditions allowing production of the amplicon, (c) isolating the antisense strand of the amplicon or the sense strand of the amplicon produced in (b), (d) if the antisense strand of the amplicon is isolated in (c), then (1) providing a first sequencing primer capable of hybridizing to the antisense strand and capable of being extended during a first nucleotide sequencing reaction, and (2) identifying, by conducting the first nucleotide sequencing reaction, the nucleotide corresponding to nucleotide 512 or 513 of SEQ ID NO:8, or if the sense strand of the amplicon is isolated in (c), then (1) providing a second sequencing primer capable of hybridizing to the sense strand and capable of being extended during a second nucleotide sequencing reaction, and (2) identifying, by conducting the second nucleotide sequencing reaction, the nucleotide corresponding to nucleotide 1536 or 1537 of SEQ ID NO:9, and (e) if the first nucleotide sequencing reaction is conducted in (d), then determining that the isolate is more tolerant to the triazole if the nucleotide corresponding to nucleotide 512 or 513 of SEQ ID NO:8 is not g, or determining that the isolate is not more tolerant to the triazole if the nucleotides corresponding to nucleotides 512 and 513 of SEQ ID NO:8 are both g, or if the second nucleotide sequencing reaction is conducted in (d), then determining that the isolate is more tolerant to the triazole if the nucleotide corresponding to nucleotide 1536 or 1537 of SEQ ID NO:9 is not c, or determining that the isolate is not more tolerant to the triazole if the nucleotides corresponding to nucleotides 1536 and 1537 of SEQ ID NO:9 are both c.

Each of the forward primer and the reverse primer is preferably from 8 to 50 nucleotides long, more preferably from 12 to 24 nucleotides long.

In (b), the forward primer advantageously is capable of hybridizing to at least a portion of a segment of the antisense strand of the amplicon, wherein the segment consists of nucleotides 1551 through 1574 of SEQ ID NO:7. Preferably, the forward primer is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, wherein the segment consists of nucleotides 1551 through 1574 of SEQ ID NO:7. More preferably, the forward primer comprises the nucleotide sequence of SEQ ID NO:16. Most preferably, the forward primer consists of the nucleotide sequence of SEQ ID NO:16.

Additionally, in (b), the reverse primer advantageously is capable of hybridizing to at least a portion of a segment of the sense strand of the amplicon, wherein the segment consists of nucleotides 720 through 743 of SEQ ID NO:6. Preferably, the reverse primer is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, wherein the segment consists of nucleotides 720 through 743 of SEQ ID NO:6. More preferably, the reverse primer comprises the nucleotide sequence of SEQ ID NO:17. Most preferably, the reverse primer consists of the nucleotide sequence of SEQ ID NO:17.

Each of the first sequencing primer and the second sequencing primer is preferably from 10 to 30 nucleotides long, more preferably from 15 to 25 nucleotides long.

The first sequencing primer advantageously is capable of hybridizing to at least a portion of a segment of the antisense strand of the amplicon, wherein the segment consists of nucleotides 1538 through 1559 of SEQ ID NO:7. Preferably, the first sequencing primer is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, wherein the segment consists of nucleotides 1538 through 1559 of SEQ ID NO:7. More preferably, the first sequencing primer comprises the nucleotide sequence of SEQ ID NO:18, SEQ ID NO:19, SEQ ID NO:20, or SEQ ID NO:21. Most preferably, the first sequencing primer consists of the nucleotide sequence of SEQ ID NO:18, SEQ ID NO:19, SEQ ID NO:20, or SEQ ID NO:21.

Additionally, the second sequencing primer advantageously is capable of hybridizing to at least a portion of a segment of the sense strand of the amplicon, wherein the segment consists of nucleotides 515 through 537 of SEQ ID NO:6. Preferably, the second sequencing is at least 50%, 51%, 52%, 53%, 54%, 55%, 56%, 57%, 58%, 59° A, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, wherein the segment consists of nucleotides 515 through 537 of SEQ ID NO:6. More preferably, the second sequencing primer comprises the nucleotide sequence of SEQ ID NO:22, SEQ ID NO:23, SEQ ID NO:24, or SEQ ID NO:25. Most preferably, the second sequencing primer consists of the nucleotide sequence of SEQ ID NO:22, SEQ ID NO:23, SEQ ID NO:24, or SEQ ID NO:25.

In preferred embodiments, in (b), the vessel contains a first oligonucleotide probe or a second oligonucleotide probe capable of detecting the amplicon produced in (b). Each of the first oligonucleotide probe and the second oligonucleotide probe is preferably from 15 to 50 nucleotides long, more preferably from 25 to 35 nucleotides long.

In more preferred embodiments, the first oligonucleotide probe is capable of hybridizing to at least a portion of a segment of the antisense strand of the amplicon, wherein the segment consists of nucleotides 1363 through 1387 of SEQ ID NO:7. Preferably, the first oligonucleotide probe is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, wherein the segment consists of nucleotides 1363 through 1387 of SEQ ID NO:7. More preferably, the first oligonucleotide probe comprises the nucleotide sequence of SEQ ID NO:26. Most preferably, the first oligonucleotide probe consists of the nucleotide sequence of SEQ ID NO:26.

Additionally, in more preferred embodiments, the second oligonucleotide probe is capable of hybridizing to at least a portion of a segment of the sense strand of the amplicon, wherein the segment consists of nucleotides 662 through 686 of SEQ ID NO:6. Preferably; the second oligonucleotide probe is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, wherein the segment consists of nucleotides 662 through 686 of SEQ ID NO:6. More preferably, the second oligonucleotide probe comprises the nucleotide sequence of SEQ ID NO:27. Most preferably, the second oligonucleotide probe consists of the nucleotide sequence of SEQ ID NO:27.

The Third Method of the Present Invention

The third method of the present invention, which is a method for determining whether an isolate of *Aspergillus fumigatus* is more tolerant to a triazole than wild-type *Aspergillus fumigatus*, comprises the following steps:

(a) providing a vessel containing a composition, wherein the composition contains a forward primer, a reverse primer, and a nucleic acid isolated from the isolate, wherein the composition is capable of amplifying, by a polymerase chain reaction, a segment of the nucleic acid to produce an amplicon, wherein production of the amplicon is primed by the forward primer and the reverse primer, wherein the amplicon encodes at least a portion of a Cyp51A protein, wherein the sense strand of the amplicon contains at least the first nucleotide of the codon corresponding to the codon encoding amino acid 138 of SEQ ID NO:3, wherein the codon encoding amino acid 138 of SEQ ID NO:3 consists of nucleotides 835, 836, and 837 of SEQ ID NO:10, wherein the reverse complement of the codon encoding amino acid 138 of SEQ ID NO:3 consists of nucleotides 1212, 1213, and 1214 of SEQ ID NO:11, (b) incubating the vessel under conditions allowing production of the amplicon, (c) isolating the antisense strand of the amplicon or the sense strand of the amplicon produced in (b), (d) if the antisense strand of the amplicon is isolated in (c), then (1) providing a first sequencing primer capable of hybridizing to the antisense strand and capable of being extended during a first nucleotide sequencing reaction, and (2) identifying, by conducting the first nucleotide sequencing reaction, the nucleotide corresponding to nucleotide 835 or 836 of SEQ ID NO:10, or if the sense strand of the amplicon is isolated in (c), then (1) providing a second sequencing primer capable of hybridizing to the sense strand and capable of being extended during a second nucleotide sequencing reaction, and (2) identifying, by conducting the second nucleotide sequencing reaction, the nucleotide corresponding to nucleotide 1213 or 1214 of SEQ ID NO:11, and (e) if the first nucleotide sequencing reaction is conducted in (d), then determining that the isolate is more tolerant to the triazole if the nucleotide corresponding to nucleotide 835 or 836 of SEQ ID NO:10 is not g, or determining that the isolate is not more tolerant to the triazole if the nucleotides corresponding to nucleotides 835 and 836 of SEQ ID NO:10 are both g, or if the second nucleotide sequencing reaction is conducted in (d), then determining that the isolate is more tolerant to the triazole if the nucleotide corresponding to nucleotide 1213 or 1214 of SEQ ID NO:11 is not c, or determining that the isolate is not more tolerant to the triazole if the nucleotides corresponding to nucleotides 1213 and 1214 of SEQ ID NO:11 are both c.

Each of the forward primer and the reverse primer is preferably from 8 to 50 nucleotides long, more preferably from 12 to 24 nucleotides long.

In (b), the forward primer advantageously is capable of hybridizing to at least a portion of a segment of the antisense strand of the amplicon, wherein the segment consists of nucleotides 1304 through 1327 or nucleotides 1257 through 1277 of SEQ ID NO:7. Preferably, the forward primer is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, wherein the segment consists of nucleotides 1304 through 1327 or nucleotides 1257 through 1277 of SEQ ID NO:7. More preferably, the forward primer comprises the nucleotide sequence of SEQ ID NO:28 or SEQ ID NO:29. Most preferably, the forward primer consists of the nucleotide sequence of SEQ ID NO:28 or SEQ ID NO:29.

Additionally, in (b), the reverse primer advantageously is capable of hybridizing to at least a portion of a segment of the sense strand of the amplicon, wherein the segment consists of nucleotides 903 through 923 of SEQ ID NO:6. Preferably, the reverse primer is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, wherein the segment consists of nucleotides 903 through 923 of SEQ ID NO:6. More preferably, the reverse primer comprises the nucleotide sequence of SEQ ID NO:30. Most preferably, the reverse primer consists of the nucleotide sequence of SEQ ID NO:30.

Each of the first sequencing primer and the second sequencing primer is preferably from 10 to 30 nucleotides long, more preferably from 15 to 25 nucleotides long.

The first sequencing primer advantageously is capable of hybridizing to at least a portion of a segment of the antisense strand of the amplicon, wherein the segment consists of nucleotides 1216 through 1235 of SEQ ID NO:7. Preferably, the first sequencing primer is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, wherein the segment consists of nucleotides 1216 through 1235 of SEQ ID NO:7. More preferably, the first sequencing primer comprises the nucleotide sequence of SEQ ID NO:31. Most preferably, the first sequencing primer consists of the nucleotide sequence of SEQ ID NO:31.

Additionally, the second sequencing primer advantageously is capable of hybridizing to at least a portion of a segment of the sense strand of the amplicon, wherein the segment consists of nucleotides 838 through 854 of SEQ ID NO:6. Preferably, the second sequencing primer is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, wherein the segment consists of nucleotides 838 through 854 of SEQ ID NO:6. More preferably, the second sequencing primer comprises the nucleotide sequence of SEQ ID NO:32. Most preferably, the second sequencing primer consists of the nucleotide sequence of SEQ ID NO:32.

In preferred embodiments, in (b), the vessel contains a first oligonucleotide probe or a second oligonucleotide probe capable of detecting the amplicon produced in (b). Each of the first oligonucleotide probe and the second oligonucleotide probe is preferably from 15 to 50 nucleotides long, more preferably from 25 to 35 nucleotides long.

In more preferred embodiments, the first oligonucleotide probe is capable of hybridizing to at least a portion of a segment of the antisense strand of the amplicon, wherein the segment consists of nucleotides 1172 through 1203 of SEQ ID NO:7. Preferably, the first oligonucleotide probe is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, wherein the segment consists of nucleotides 1172 through 1203 of SEQ ID NO:7. More preferably, the first oligonucleotide probe comprises the nucleotide sequence of SEQ ID NO:33. Most preferably, the first oligonucleotide probe consists of the nucleotide sequence of SEQ ID NO:33.

Additionally, in more preferred embodiments, the second oligonucleotide probe is capable of hybridizing to at least a portion of a segment of the sense strand of the amplicon, wherein the segment consists of nucleotides 846 through 877 of SEQ ID NO:6. Preferably, the second oligonucleotide probe is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, wherein the segment consists of nucleotides 846 through 877 of SEQ ID NO:6. More preferably, the second oligonucleotide probe comprises the nucleotide sequence of SEQ ID NO:34. Most preferably, the second oligonucleotide probe consists of the nucleotide sequence of SEQ ID NO:34.

The Fourth Method of the Present Invention

The fourth method of the present invention, which is a method for determining whether an isolate of *Aspergillus fumigatus* is more tolerant to a triazole than wild-type *Aspergillus fumigatus*, comprises the following steps:

(a) providing a vessel containing a composition, wherein the composition contains a forward primer, a reverse primer, and a nucleic acid isolated from the isolate, wherein the composition is capable of amplifying, by a polymerase chain reaction, a segment of the nucleic acid to produce an amplicon, wherein production of the amplicon is primed by the forward primer and the reverse primer, wherein the amplicon encodes at least a portion of a Cyp51A protein, wherein the sense strand of the amplicon contains at least the first nucleotide of the codon corresponding to the codon encoding amino acid 220 of SEQ ID NO:4, wherein the codon encoding amino acid 220 of SEQ ID NO:4 consists of nucleotides 1081, 1082, and 1083 of SEQ ID NO:12, wherein the reverse complement of the codon encoding amino acid 220 of SEQ ID NO:4 consists of nucleotides 966, 967, and 968 of SEQ ID NO:13, (b) incubating the vessel under conditions allowing production of the amplicon, (c) isolating the antisense strand of the amplicon or the sense strand of the amplicon produced in (b), (d) if the antisense strand of the amplicon is isolated in (c), then (1) providing a first sequencing primer capable of hybridizing to the antisense strand and capable of being extended during a first nucleotide sequencing reaction, and (2) identifying, by conducting the first nucleotide sequencing reaction, the nucleotide corresponding to nucleotide 1081, 1082, or 1083 of SEQ ID NO:12, or if the sense strand of the amplicon is isolated in (c), then (1) providing a second sequencing primer capable of hybridizing to the sense strand and capable of being extended during a second nucleotide sequencing reaction, and (2) identifying, by conducting the second nucleotide sequencing reaction, the nucleotide corresponding to nucleotide 966, 967, or 968 of SEQ ID NO:13, and (e) if the first nucleotide sequencing reaction is conducted in (d), then determining that the isolate is more tolerant to the triazole if the nucleotide corresponding to nucleotide 1081, 1082, or 1083 of SEQ ID NO:12 is not a, t, or g, respectively, or determining that the isolate is not more tolerant to the triazole if the nucleotides corresponding to nucleotides 1081, 1082, and 1083 of SEQ ID NO:12 are a, t, and g, respectively, or if the second nucleotide sequencing reaction is conducted in (d), then determining that the isolate is more tolerant to the triazole if the nucleotide corresponding to nucleotide 966, 967, or 968 of SEQ ID NO:13 is not c, a, or t, respectively, or determining that the isolate is not more tolerant to the triazole if the nucleotides corresponding to nucleotides 966, 967, and 968 of SEQ ID NO:13 are c, a, and t, respectively.

Each of the forward primer and the reverse primer is preferably from 8 to 50 nucleotides long, more preferably from 12 to 24 nucleotides long.

In (b), the forward primer advantageously is capable of hybridizing to at least a portion of a segment of the antisense strand of the amplicon, wherein the segment consists of nucleotides 1062 through 1084 or nucleotides 983 through 1002 of SEQ ID NO:7. Preferably, the forward is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide, and wherein the segment consists of nucleotides 1062 through 1084 or nucleotides 983 through 1002 of SEQ ID NO:7. More preferably, the forward primer comprises the nucleotide sequence of SEQ ID NO:35 or SEQ ID NO:36. Most preferably, the forward primer consists of the nucleotide sequence of SEQ ID NO:35 or SEQ ID NO:36.

Additionally, in (b), the reverse primer advantageously is capable of hybridizing to at least a portion of a segment of the sense strand of the amplicon, wherein the segment consists of nucleotides 1212 through 1235 or nucleotides 1107 through 1129 of SEQ ID NO:6. Preferably, the reverse primer is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, wherein the segment consists of nucleotides 1212 through 1235 or nucleotides 1107 through 1129 of SEQ ID NO:6. More preferably, the reverse primer comprises the nucleotide sequence of SEQ ID NO:37 or SEQ ID NO:38. Most preferably, the reverse primer consists of the nucleotide sequence of SEQ ID NO:37 or SEQ ID NO:38.

Each of the first sequencing primer and the second sequencing primer is preferably from 10 to 30 nucleotides long, more preferably from 15 to 25 nucleotides long.

The first sequencing primer advantageously is capable of hybridizing to at least a portion of a segment of the antisense strand of the amplicon, wherein the segment consists of nucleotides 972 through 989 of SEQ ID NO:7. Preferably, the first sequencing primer is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, wherein the segment consists of 972 through 989 of SEQ ID NO:7. More preferably, the first sequencing primer comprises the nucleotide sequence of SEQ ID NO:39. Most preferably, the first sequencing primer consists of the nucleotide sequence of SEQ ID NO:39.

Additionally, the second sequencing primer advantageously is capable of hybridizing to at least a portion of a segment of the sense strand of the amplicon, wherein the segment consists of nucleotides 1085 through 1099 of SEQ ID NO:6. Preferably, the second sequencing primer is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, wherein the segment consists of nucleotides 1085 through 1099 of SEQ ID NO:6. More preferably, the second sequencing primer comprises the nucleotide sequence of SEQ ID NO:40. Most preferably, the second sequencing primer consists of the nucleotide sequence of SEQ ID NO:40.

In preferred embodiments, in (b), the vessel contains a first oligonucleotide probe or a second oligonucleotide probe capable of detecting the amplicon produced in (b). Each of the first oligonucleotide probe and the second oligonucleotide probe is preferably from 15 to 50 nucleotides long, more preferably from 25 to 35 nucleotides long.

In more preferred embodiments, the first oligonucleotide probe is capable of hybridizing to at least a portion of a segment of the antisense strand of the amplicon, wherein the segment consists of nucleotides 954 through 979 of SEQ ID NO:13. Preferably, the first oligonucleotide probe is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, wherein the segment consists of nucleotides 954 through 979 of SEQ ID NO:13. More preferably, the first oligonucleotide probe comprises the nucleotide sequence of SEQ ID NO:41. Most preferably, the first oligonucleotide probe consists of the nucleotide sequence of SEQ ID NO:41. Advantageously, nucleotides 12, 13, and 14 of SEQ ID NO:41 are a, t, and g, respectively.

Additionally, in more preferred embodiments, the second oligonucleotide probe is capable of hybridizing to at least a portion of a segment of the sense strand of the amplicon, wherein the segment consists of nucleotides 1070 through 1095 of SEQ ID NO:12. Preferably, the second oligonucleotide probe is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, wherein the segment consists of nucleotides 1070 through 1095 of SEQ ID NO:12. More preferably, the second oligonucleotide probe comprises the nucleotide sequence of SEQ ID NO:42. Most preferably, the second oligonucleotide probe consists of the nucleotide sequence of SEQ ID NO:42. Advantageously, nucleotides 13, 14, and 15 of SEQ ID NO:42 are c, a, and t, respectively.

The Fifth Method of the Present Invention

The fifth method of the present invention, which is a method for determining whether an isolate of *Aspergillus fumigatus* is more tolerant to a triazole than wild-type *Aspergillus fumigatus*, comprises the following steps:

(a) providing a vessel containing a composition, wherein the composition contains a forward primer, a reverse primer, and a nucleic acid isolated from the isolate, wherein the composition is capable of amplifying, by a polymerase chain reaction, a segment of the nucleic acid to produce an amplicon, wherein production of the amplicon is primed by the forward primer and the reverse primer, wherein the amplicon encodes at least a portion of a Cyp51A protein, wherein the sense strand of the amplicon contains at least the first nucleotide of the codon corresponding to the codon encoding amino acid 448 of SEQ ID NO:5, wherein the codon encoding amino acid 448 of SEQ ID NO:5 consists of nucleotides 1765, 1766, and 1767 of SEQ ID NO:14, wherein the reverse complement of the codon encoding amino acid 448 of SEQ ID NO:5 consists of nucleotides 282, 283, and 284 of SEQ ID NO:15, (b) incubating the vessel under conditions allowing production of the amplicon, (c) isolating the antisense strand of the amplicon or the sense strand of the amplicon produced in (b), (d) if the antisense strand of the amplicon is isolated in (c), then (1) providing a first sequencing primer capable of hybridizing to the antisense strand and capable of being extended during a first nucleotide sequencing reaction, and (2) identifying, by conducting the first nucleotide sequencing reaction, the nucleotide corresponding to nucleotide 1765 or 1766 of SEQ ID NO:14, or if the sense strand of the amplicon is isolated in (c), then (1) providing a second sequencing primer capable of hybridizing to the sense strand and capable of being extended during a second nucleotide sequencing reaction, and (2) identifying, by conducting the second nucleotide sequencing reaction, the nucleotide corresponding to nucleotide 283 or 284 of SEQ ID NO:15, and (e) if the first nucleotide sequencing reaction is conducted in (d), then determining that the isolate is more tolerant to the triazole if the nucleotide corresponding to nucleotide 1765 or 1766 of SEQ ID NO:14 is not g, or determining that the isolate is not more tolerant to the triazole if the nucleotides corresponding to nucleotides 1765 and 1766 of SEQ ID NO:14 are both g, or if the second nucleotide sequencing reaction is conducted in (d), then determining that the isolate is more tolerant to the triazole if the nucleotide corresponding to nucleotide 283 or 284 of SEQ ID NO:15 is not c, or determining that the isolate is not more tolerant to the triazole if the nucleotides corresponding to nucleotides 283 and 284 of SEQ ID NO:15 are both c.

Each of the forward primer and the reverse primer is preferably from 8 to 50 nucleotides long, more preferably from 12 to 24 nucleotides long.

In (b), the forward primer advantageously is capable of hybridizing to at least a portion of a segment of the antisense strand of the amplicon, wherein the segment consists of nucleotides 352 through 374 of SEQ ID NO:7. Preferably, the forward primer is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, wherein the segment consists of nucleotides 352 through 374 of SEQ ID NO:7. More preferably, the forward primer comprises the nucleotide sequence of SEQ ID NO:43. Most preferably, the forward primer consists of the nucleotide sequence of SEQ ID NO:43.

Additionally, in (b), the reverse primer advantageously is capable of hybridizing to at least a portion of a segment of the sense strand of the amplicon, wherein the segment consists of nucleotides 1784 through 1804 of SEQ ID NO:6. Preferably, the reverse primer is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, wherein the segment consists of nucleotides 1784 through 1804 of SEQ ID NO:6. More preferably, the reverse primer comprises the nucleotide sequence of SEQ ID NO:44 or SEQ ID NO:45. Most preferably, the reverse primer consists of the nucleotide sequence of SEQ ID NO:44 or SEQ ID NO:45.

Each of the first sequencing primer and the second sequencing primer is preferably from 10 to 30 nucleotides long, more preferably from 15 to 25 nucleotides long.

The first sequencing primer advantageously is capable of hybridizing to at least a portion of a segment of the antisense strand of the amplicon, wherein the segment consists of nucleotides 288 through 304 of SEQ ID NO:7. Preferably, the first sequencing primer is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, wherein the segment consists of nucleotides 288 through 304 of SEQ ID NO:7. More preferably, the first sequencing primer comprises the nucleotide sequence of SEQ ID NO:46. Most preferably, the first sequencing primer consists of the nucleotide sequence of SEQ ID NO:46.

Additionally, the second sequencing primer advantageously is capable of hybridizing to at least a portion of a segment of the sense strand of the amplicon, wherein the segment consists of nucleotides 1769 through 1783 of SEQ ID NO:6. Preferably, the second sequencing primer is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, wherein the segment consists of nucleotides 1769 through 1783 of SEQ ID NO:6. More preferably, the second sequencing primer comprises the nucleotide sequence of SEQ ID NO:47. Most preferably, the second sequencing primer consists of the nucleotide sequence of SEQ ID NO:47.

In preferred embodiments, in (b), the vessel contains a first oligonucleotide probe or a second oligonucleotide probe capable of detecting the amplicon produced in (b). Each of the first oligonucleotide probe and the second oligonucleotide probe is preferably from 15 to 50 nucleotides long, more preferably from 25 to 35 nucleotides long.

In more preferred embodiments, the first oligonucleotide probe is capable of hybridizing to at least a portion of a segment of the antisense strand of the amplicon, wherein the segment consists of nucleotides 274 through 295 of SEQ ID NO:15. Preferably, the first oligonucleotide probe is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, wherein the segment consists of nucleotides 274 through 295 of SEQ ID NO:15. More preferably, the first oligonucleotide probe comprises the nucleotide sequence of SEQ ID NO:48. Most preferably, the first oligonucleotide probe consists of the nucleotide sequence of SEQ ID NO:48. Advantageously, nucleotides 12, 13, and 14 of SEQ ID NO:48 are g, g, and t, respectively.

Additionally, in more preferred embodiments, the second oligonucleotide probe is capable of hybridizing to at least a portion of a segment of the sense strand of the amplicon, wherein the segment consists of nucleotides 1754 through 1775 of SEQ ID NO:14. Preferably, the second oligonucleotide probe is at least 50%, 51%, 52%, 53%, 54%, 55%, 56%, 57%, 58%, 59%; 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, wherein the segment consists of nucleotides 1754 through 1775 of SEQ ID NO:14. More preferably, the second oligonucleotide probe comprises the nucleotide sequence of SEQ ID NO:49. Most preferably, the second oligonucleotide probe consists of the nucleotide sequence of SEQ ID NO:49. Advantageously, nucleotides 9, 10, and 11 of SEQ ID NO:49 are a, c, and c, respectively.

BRIEF DESCRIPTION OF THE DRAWINGS

FIG. 1A illustrates normalized fluorescence curves of the positive-control plasmid containing a 269 base pair-long fragment of cyp51A of *Aspergillus fumigatus*, which was quantified using PicoGreen and diluted 10-fold from $10^8$ to 10 copies per reaction in the presence of 500 ng of human DNA (respective $C_T$ curves for each 10-fold dilution, in duplicate, from left to right; $r^2$=0.997). FIG. 1B shows normalized fluorescence curves of three concentrations of the positive-control plasmid (dashed curves; $r^2$=0.999), a negative control, and 32 DNA extracts from whole-blood samples. One positive specimen (solid curve) was detected with a calculated concentration of nine copies per reaction.

FIG. 2A shows a pyrogram illustrating a pyrosequencing analysis of an amplicon generated by the polymerase chain reaction from a wild-type *Aspergillus fumigatus* isolate. FIG. 2B shows a pyrogram illustrating a pyrosequencing analysis of an amplicon generated by the polymerase chain reaction from the positive clinical sample described in FIG. 1B. The best-quality sequence is presented under each pyrogram, and the codon encoding amino acid 54 is boxed. The nucleotide sequence illustrated in FIG. 2A is shown in the Sequence Listing as SEQ ID NO: 50, and the nucleotide sequence illustrated in FIG. 2B is shown in the Sequence Listing as SEQ ID NO: 51.

DETAILED DESCRIPTION

Figure 1:
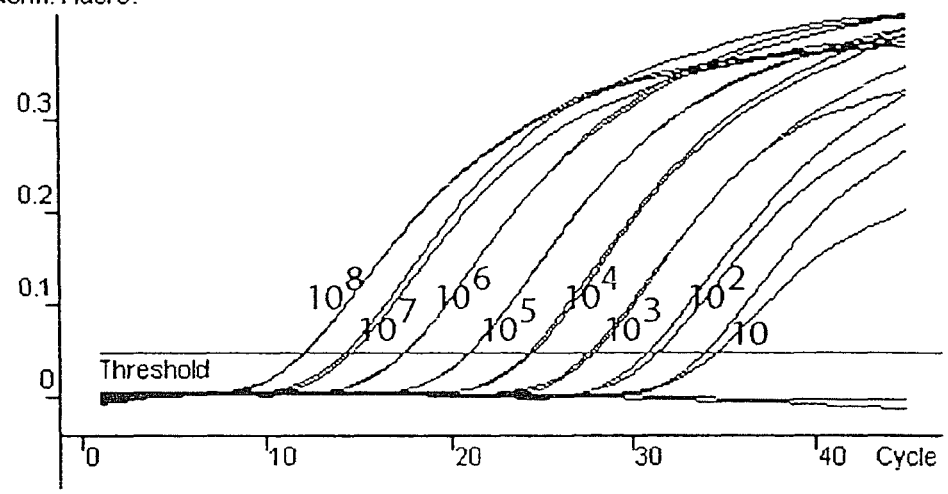
FIG. 1 shows a positive-control plasmid-dilution detection range and analysis of clinical samples by real-time polymerase chain reactions.
Figure 1:
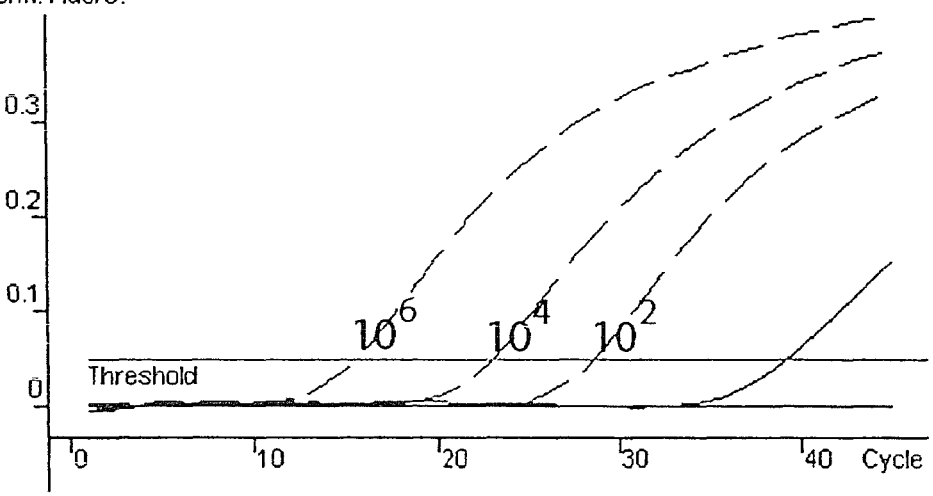

The following examples are examples of the first and second methods of the present invention. Specifically, these examples illustrate the use of (a) two specific oligonucleotides of the present invention (i.e., one forward primer and one reverse primer) to produce an amplicon specific to cyp51A of *Aspergillus fumigatus* by the polymerase chain reaction using nucleic acid isolated from a sample as a template, (b) a specific oligonucleotide of the present invention (i.e., probe) to detect this amplicon, thereby determining that an isolate of *Aspergillus fumigatus* was present in the sample, and (c) a specific oligonucleotide of the present invention (i.e., a sequencing primer) to determine that the identity of amino acid 54 of Cyp51A protein is Gly. These examples are set forth by way of illustration only, and nothing therein shall be taken as a limitation upon the overall scope of the invention.

EXAMPLES

A region of cyp51A of *Aspergillus fumigatus* 269 base pairs in length was amplified using the Rotor-Gene 3000 platform (Corbett Research, Sydney, Australia). A dual-labeled DNA probe was employed for real-time monitoring of amplification by the polymerase chain reaction (PCR). The PCRs were carried out in a volume of 25 µl containing a 300 nM concentration of each primer (forward primer: 5'-TCATTGGGTCCCATTTCTGGGTAG-3' (SEQ ID NO: 16), reverse primer: 5'-biotin/TAGACCTCTTCCGCATTGA-CATCC-3' (SEQ ID NO: 17) with the addition of a biotin moiety), 100 nM probe (5'-6-FAM/AAACCACAGTCTAC-CTGGGCGTTCA/BHQ-1-3') (nucleotide sequence of SEQ ID NO:26 with the addition of a 6-FAM moiety and a BHQ-1 moiety, wherein the 6-FAM moiety is 6-carboxy-fluorescein and the BHQ-1 moiety is Black Hole Quencher 1), and 12.5 µl of a 2× concentration of Platinum Quantitative PCR Supermix-UDG (Invitrogen, Carlsbad, Calif.). Parameters for the PCRs were as follows: an initial incubation at 50° C. for 2 minutes for UDG activity followed by 95° C. for 2 minutes to inactivate the UDG and activate the Taq DNA polymerase. Next, 45 cycles of denaturation (95° C., 20 seconds) and annealing and extension (60° C., 60 seconds) were performed with fluorescence acquisition (excitation, 470 nM; emission, 510 nM) immediately following each annealing-extension step. A final extension (72° C., 10 minutes) was performed.

Fluorescence curves were analyzed with dynamic-tube normalization, slope correction, and automatic threshold determination by a best-fit line of at least three standards using Rotor-Gene version 5.0 software (Corbett Research, Sydney, Australia). The specificity of the real-time PCR was assessed by carrying out the reaction with DNA from a panel of 44 different species of viral, bacterial, and fungal pathogens, including *Aspergillus fumigatus* SRRC 2006, *Aspergillus flavus* MC 21, *Aspergillus nidulans* NRRL 187, *Aspergillus niger* SN 26, *Aspergillus oryzae* NRRL 1989, *Aspergillus terreus* NRRL 255, and *Aspergillus versicolor* NRRL 238. All isolated cultures were purchased from the American Type Culture Collection, Manassas, Va. DNA was extracted using standard methods described in Ausubel et al., 1997, Short Protocols in Molecular Biology, $3^{rd}$ edition, John Wiley & Sons, Inc., New York, N.Y. Only DNA from *Aspergillus fumigatus* was amplified (data not shown).

A positive-control plasmid was constructed by subcloning, into the pCR II-TOPO vector (Invitrogen, Carlsbad, Calif.), the amplicon generated by PCR using genomic DNA extracted from isolated *Aspergillus fumigatus* as a template. The linear detection range was from $10^8$ to 10 copies of positive-control plasmid per reaction in the presence of 500 ng of DNA extracted from *Aspergillus*-negative whole-blood samples (see FIG. 1A). All extractions of whole blood were performed as described in Van Burik et al., 1998, Panfungal PCR assay for detection of fungal infection in human blood specimens. Journal of Clinical Microbiology 36:1169-1175, the entire contents of which are hereby incorporated by reference. The real-time PCR was also able to detect 50 μg of mycelia from a freeze-dried culture of *Aspergillus fumigatus* (purchased from the American Type Culture Collection, Manassas, Va.) spiked into 1-ml whole-blood samples from two healthy donors with no clinical symptoms of aspergillosis, using the donors' nonspiked whole blood as negative controls (data not shown).

To assess the functionality of the real-time PCR with actual clinical samples, DNA extracts from 56 whole-blood samples obtained from different patients and three dilutions of the positive-control plasmid were used as templates (see FIG. 1B). *Aspergillus fumigatus* DNA was detected in 2 of the 56 samples, which correlates with the results obtained from an independent *Aspergillus fumigatus* conventional PCR assay targeting the 26S/internal transcribed spacer rRNA gene region as described in Spreadbury et al., 1993, Detection of *Aspergillus fumigatus* by polymerase chain reaction. Journal of Clinical Microbiology 31:615-621. Neither PCR assay generated a positive result for the other 54 samples. The quality of clinical-sample DNA and the absence of PCR inhibitors were validated by amplification of the human glyceraldehyde-3-phosphate dehydrogenase gene by real-time PCR (Biosearch Technologies, Novato, Calif.) (data not shown).

The nucleotide sequences of amplicons generated from real-time PCR were determined using a bioluminometric, nonelectrophoretic technique called pyrosequencing, which utilizes a cascade of coupled enzymatic reactions to monitor DNA synthesis. The pyrosequencing method is described in U.S. Pat. Nos. 6,210,891 and 6,258,568, wherein the entire contents of both patents are hereby incorporated by reference, and Ronaghi et al., 1998, A sequencing method based on real-time pyrophosphate. Science 281:363-365, the entire contents of which are hereby incorporated by reference. The pyrosequencing technique has the advantages of speed, accuracy, and parallel processing. The 5' end of the reverse primer used in the PCR was biotinylated to facilitate amplicon capture and preparation for pyrosequencing directly from the PCR using streptavidin Sephadex (Amersham Biosciences, Uppsala, Sweden) and the Pyrosequencing Vacuum Prep tool (Biotage, Uppsala, Sweden).

Figure 2:
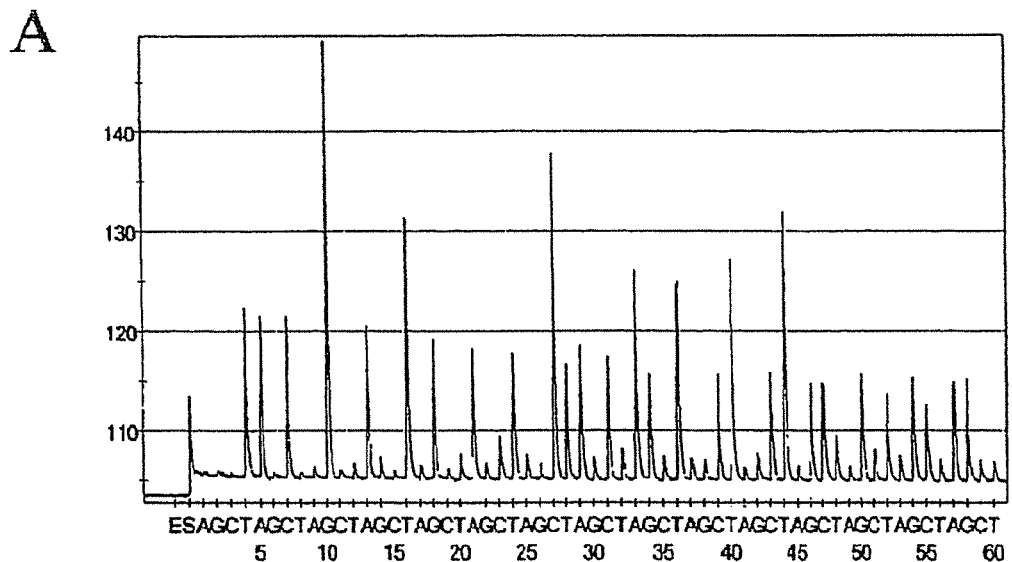
FIG. 2 illustrates representative pyrosequencing data, in diagrams called pyrograms, from positive controls and clinical samples.
Figure 2:
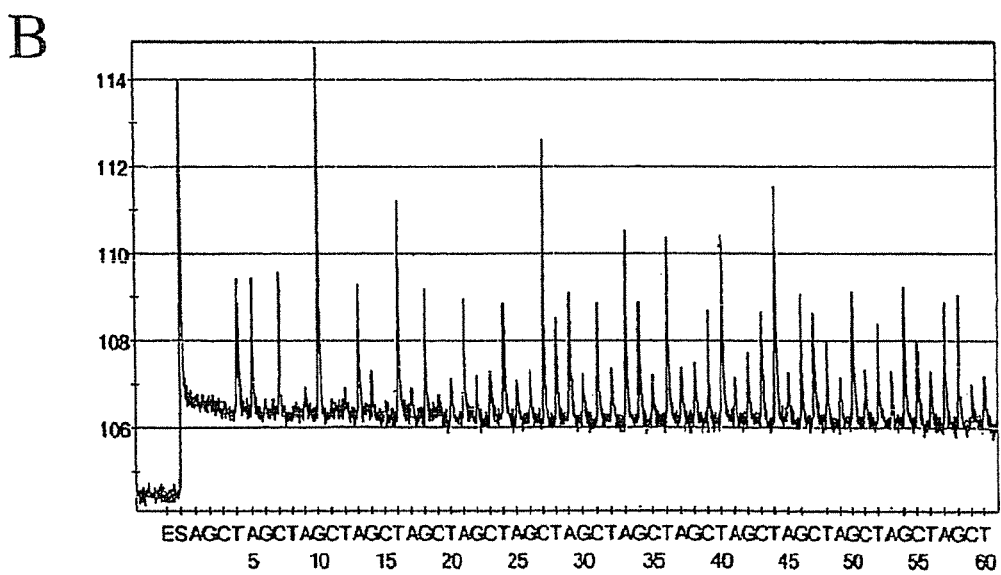

For the pyrosequencing reaction, a 0.5 nM concentration of the sequencing primer (5'-TCTGGGTAGTACCATCAGT-3') (SEQ ID NO:18) was used. This sequencing primer possesses a unique sequence found within the amplicon upstream from the codon which encodes the amino acid corresponding to the amino acid at position 54 of the Cyp51A protein. A Pyrosequencing 96MA System (Biotage, Uppsala, Sweden) was programmed with 10 cycles of an AGCT dispensation order. The resulting pyrosequencing data was analyzed with the PSQ 96MA version 2.1 software (Biotage, Uppsala, Sweden). The best-quality DNA sequences resolved were used in subsequent analyses. Typically, 19 to 24 bases of sequence were interpretable when genomic DNA extracted from isolated *Aspergillus fumigatus* was used (see FIG. 2A). The lengths of the best-quality sequences were significantly shorter from clinical samples but provided enough sequence to identify the target and determine the codon for the amino acid at position 54 (see FIG. 2B). All nucleotide sequences obtained by pyrosequencing were identical to the expected nucleotide sequence of cyp51A of *Aspergillus fumigatus*.

The data presented in these examples justify expansion of the pyrosequencing analysis of cyp51A to determine other sites of mutation conferring tolerance to triazoles, including the codons encoding amino acids corresponding to the amino acid at position 138 of SEQ ID NO:3 (as described in the third method of the present invention), the amino acid at position 220 of SEQ ID NO:4 (as described in the fourth method of the present invention), and the amino acid at position 448 of SEQ ID NO:5 (as described in the fifth method of the present invention). Nucleotide sequences of oligonucleotides potentially useful as forward and reverse primers, probes, and nucleotide sequencing primers are determined using computer programs such as Assay Design Software 1.0.6 (Biotage, Uppsala, Sweden) and Beacon Designer 4.02 (Build 402003) (PREMIER Biosoft International, Palo Alto, Calif.).

What is claimed is:

1. A method for determining the presence of *Aspergillus fumigatus* in whole blood of a human and whether said *Aspergillus fumigatus* is more tolerant to triazole than wild-type *Aspergillus fumigatus*, comprising the steps of:
   (a) obtaining whole blood from a human subject, wherein said human subject is suspected of infection with triazole-resistant *Aspergillus fumigatus*;
   (b) extracting DNA from said whole blood;
   (c) performing a real-time PCR on said extracted DNA using a forward primer consisting of the nucleotide sequence SEQ ID NO: 16, a reverse primer consisting of the nucleotide sequence SEQ ID NO: 17 and a probe consisting of the nucleotide sequence SEQ ID NO: 26 to generate an amplicon, wherein the generation of said amplicon in said real-time PCR is indicative of the presence of *Aspergillus fumigatus*;
   (d) isolating said generated amplicon;
   (e) performing a pyrosequencing reaction on said isolated amplicon using a sequencing primer consisting of the nucleotide sequence SEQ ID NO: 18; and
   (f) determining the identity of the nucleotides encoding the amino acid at position 54 of the Cyp51A protein, wherein the presence of an amino acid other than glycine at said position 54 is indicative of the presence of said *Aspergillus fumigatus* that is more tolerant to triazole than wild-type *Aspergillus fumigatus*.

2. The method of claim 1, wherein said probe is dual-florescence labeled to detect said generated amplicon.

3. The method of claim 1, wherein said reverse primer is biotinylated at its 5' end to facilitate said isolation of said generated amplicon.

* * * * *

SEQUENCE LISTING

<160> NUMBER OF SEQ ID NOS: 51

<210> SEQ ID NO 1
<211> LENGTH: 515
<212> TYPE: PRT
<213> ORGANISM: Aspergillus fumigatus

<400> SEQUENCE: 1

Met Val Pro Met Leu Trp Leu Thr Ala Tyr Met Ala Val Ala Val Leu
1                 5                 10               15

```
Thr Ala Ile Leu Leu Asn Val Val Tyr Gln Leu Phe Arg Leu Trp
            20                  25                  30

Asn Arg Thr Glu Pro Pro Met Val Phe His Trp Val Pro Phe Leu Gly
        35                  40                  45

Ser Thr Ile Ser Tyr Gly Ile Asp Pro Tyr Lys Phe Phe Ala Cys
50                  55                  60

Arg Glu Lys Tyr Gly Asp Ile Phe Thr Phe Ile Leu Leu Gly Gln Lys
65                  70                  75                  80

Thr Thr Val Tyr Leu Gly Val Gln Gly Asn Glu Phe Ile Leu Asn Gly
                85                  90                  95

Lys Leu Lys Asp Val Asn Ala Glu Glu Val Tyr Ser Pro Leu Thr Thr
            100                 105                 110

Pro Val Phe Gly Ser Asp Val Val Tyr Asp Cys Pro Asn Ser Lys Leu
            115                 120                 125

Met Glu Gln Lys Lys Phe Ile Lys Tyr Gly Leu Thr Gln Ser Ala Leu
130                 135                 140

Glu Ser His Val Pro Leu Ile Glu Lys Glu Val Leu Asp Tyr Leu Arg
145                 150                 155                 160

Asp Ser Pro Asn Phe Gln Gly Ser Ser Gly Arg Met Asp Ile Ser Ala
                165                 170                 175

Ala Met Ala Glu Ile Thr Ile Phe Thr Ala Ala Arg Ala Leu Gln Gly
            180                 185                 190

Gln Glu Val Arg Ser Lys Leu Thr Ala Glu Phe Ala Asp Leu Tyr His
            195                 200                 205

Asp Leu Asp Lys Gly Phe Thr Pro Ile Asn Phe Met Leu Pro Trp Ala
        210                 215                 220

Pro Leu Pro His Asn Lys Lys Arg Asp Ala Ala His Ala Arg Met Arg
225                 230                 235                 240

Ser Ile Tyr Val Asp Ile Ile Asn Gln Arg Arg Leu Asp Gly Asp Lys
                245                 250                 255

Asp Ser Gln Lys Ser Asp Met Ile Trp Asn Leu Met Asn Cys Thr Tyr
            260                 265                 270

Lys Asn Gly Gln Gln Val Pro Asp Lys Glu Ile Ala His Met Met Ile
            275                 280                 285

Thr Leu Leu Met Ala Gly Gln His Ser Ser Ser Ser Ile Ser Ala Trp
        290                 295                 300

Ile Met Leu Arg Leu Ala Ser Gln Pro Lys Val Leu Glu Glu Leu Tyr
305                 310                 315                 320

Gln Glu Gln Leu Ala Asn Leu Gly Pro Ala Gly Pro Asp Gly Ser Leu
                325                 330                 335

Pro Pro Leu Gln Tyr Lys Asp Leu Asp Lys Leu Pro Phe His Gln His
            340                 345                 350

Val Ile Arg Glu Thr Leu Arg Ile His Ser Ser Ile His Ser Ile Met
            355                 360                 365

Arg Lys Val Lys Ser Pro Leu Pro Val Pro Gly Thr Pro Tyr Met Ile
        370                 375                 380

Pro Pro Gly Arg Val Leu Leu Ala Ser Pro Gly Val Thr Ala Leu Ser
385                 390                 395                 400

Asp Glu His Phe Pro Asn Ala Gly Cys Trp Asp Pro His Arg Trp Glu
                405                 410                 415

Asn Gln Ala Thr Lys Glu Gln Glu Asn Asp Glu Val Val Asp Tyr Gly
            420                 425                 430
```

```
Tyr Gly Ala Val Ser Lys Gly Thr Ser Ser Pro Tyr Leu Pro Phe Gly
            435                 440                 445

Ala Gly Arg His Arg Cys Ile Gly Glu Lys Phe Ala Tyr Val Asn Leu
450                 455                 460

Gly Val Ile Leu Ala Thr Ile Val Arg His Leu Arg Leu Phe Asn Val
465                 470                 475                 480

Asp Gly Lys Lys Gly Val Pro Glu Thr Asp Tyr Ser Ser Leu Phe Ser
                485                 490                 495

Gly Pro Met Lys Pro Ser Ile Ile Gly Trp Glu Lys Arg Ser Lys Asn
                500                 505                 510

Thr Ser Lys
        515

<210> SEQ ID NO 2
<211> LENGTH: 515
<212> TYPE: PRT
<213> ORGANISM: Aspergillus fumigatus
<220> FEATURE:
<221> NAME/KEY: misc_feature
<222> LOCATION: (54)..(54)
<223> OTHER INFORMATION: Xaa can be any naturally occurring amino acid

<400> SEQUENCE: 2

Met Val Pro Met Leu Trp Leu Thr Ala Tyr Met Ala Val Ala Val Leu
1               5                   10                  15

Thr Ala Ile Leu Leu Asn Val Val Tyr Gln Leu Phe Phe Arg Leu Trp
            20                  25                  30

Asn Arg Thr Glu Pro Pro Met Val Phe His Trp Val Pro Phe Leu Gly
        35                  40                  45

Ser Thr Ile Ser Tyr Xaa Ile Asp Pro Tyr Lys Phe Phe Ala Cys
    50                  55                  60

Arg Glu Lys Tyr Gly Asp Ile Phe Thr Phe Ile Leu Leu Gly Gln Lys
65                  70                  75                  80

Thr Thr Val Tyr Leu Gly Val Gln Gly Asn Glu Phe Ile Leu Asn Gly
                85                  90                  95

Lys Leu Lys Asp Val Asn Ala Glu Glu Val Tyr Ser Pro Leu Thr Thr
            100                 105                 110

Pro Val Phe Gly Ser Asp Val Val Tyr Asp Cys Pro Asn Ser Lys Leu
        115                 120                 125

Met Glu Gln Lys Lys Phe Ile Lys Tyr Gly Leu Thr Gln Ser Ala Leu
130                 135                 140

Glu Ser His Val Pro Leu Ile Glu Lys Glu Val Leu Asp Tyr Leu Arg
145                 150                 155                 160

Asp Ser Pro Asn Phe Gln Gly Ser Ser Gly Arg Met Asp Ile Ser Ala
                165                 170                 175

Ala Met Ala Glu Ile Thr Ile Phe Thr Ala Ala Arg Ala Leu Gln Gly
            180                 185                 190

Gln Glu Val Arg Ser Lys Leu Thr Ala Glu Phe Ala Asp Leu Tyr His
        195                 200                 205

Asp Leu Asp Lys Gly Phe Thr Pro Ile Asn Phe Met Leu Pro Trp Ala
210                 215                 220

Pro Leu Pro His Asn Lys Lys Arg Asp Ala Ala His Ala Arg Met Arg
225                 230                 235                 240

Ser Ile Tyr Val Asp Ile Ile Asn Gln Arg Arg Leu Asp Gly Asp Lys
                245                 250                 255

Asp Ser Gln Lys Ser Asp Met Ile Trp Asn Leu Met Asn Cys Thr Tyr
```

```
                    260                 265                 270
Lys Asn Gly Gln Gln Val Pro Asp Lys Glu Ile Ala His Met Met Ile
            275                 280                 285

Thr Leu Leu Met Ala Gly Gln His Ser Ser Ser Ile Ser Ala Trp
        290                 295                 300

Ile Met Leu Arg Leu Ala Ser Gln Pro Lys Val Leu Glu Glu Leu Tyr
305                 310                 315                 320

Gln Glu Gln Leu Ala Asn Leu Gly Pro Ala Gly Pro Asp Gly Ser Leu
                325                 330                 335

Pro Pro Leu Gln Tyr Lys Asp Leu Asp Lys Leu Pro Phe His Gln His
            340                 345                 350

Val Ile Arg Glu Thr Leu Arg Ile His Ser Ser Ile His Ser Ile Met
        355                 360                 365

Arg Lys Val Lys Ser Pro Leu Pro Val Pro Gly Thr Pro Tyr Met Ile
370                 375                 380

Pro Pro Gly Arg Val Leu Leu Ala Ser Pro Gly Val Thr Ala Leu Ser
385                 390                 395                 400

Asp Glu His Phe Pro Asn Ala Gly Cys Trp Asp Pro His Arg Trp Glu
                405                 410                 415

Asn Gln Ala Thr Lys Glu Gln Glu Asn Asp Glu Val Val Asp Tyr Gly
            420                 425                 430

Tyr Gly Ala Val Ser Lys Gly Thr Ser Ser Pro Tyr Leu Pro Phe Gly
        435                 440                 445

Ala Gly Arg His Arg Cys Ile Gly Glu Lys Phe Ala Tyr Val Asn Leu
    450                 455                 460

Gly Val Ile Leu Ala Thr Ile Val Arg His Leu Arg Leu Phe Asn Val
465                 470                 475                 480

Asp Gly Lys Lys Gly Val Pro Glu Thr Asp Tyr Ser Ser Leu Phe Ser
                485                 490                 495

Gly Pro Met Lys Pro Ser Ile Ile Gly Trp Glu Lys Arg Ser Lys Asn
            500                 505                 510

Thr Ser Lys
        515

<210> SEQ ID NO 3
<211> LENGTH: 515
<212> TYPE: PRT
<213> ORGANISM: Aspergillus fumigatus
<220> FEATURE:
<221> NAME/KEY: misc_feature
<222> LOCATION: (138)..(138)
<223> OTHER INFORMATION: Xaa can be any naturally occurring amino acid

<400> SEQUENCE: 3

Met Val Pro Met Leu Trp Leu Thr Ala Tyr Met Ala Val Ala Val Leu
1               5                   10                  15

Thr Ala Ile Leu Leu Asn Val Val Tyr Gln Leu Phe Phe Arg Leu Trp
            20                  25                  30

Asn Arg Thr Glu Pro Pro Met Val Phe His Trp Val Pro Phe Leu Gly
        35                  40                  45

Ser Thr Ile Ser Tyr Gly Ile Asp Pro Tyr Lys Phe Phe Phe Ala Cys
    50                  55                  60

Arg Glu Lys Tyr Gly Asp Ile Phe Thr Phe Ile Leu Leu Gly Gln Lys
65                  70                  75                  80

Thr Thr Val Tyr Leu Gly Val Gln Gly Asn Glu Phe Ile Leu Asn Gly
                85                  90                  95
```

```
Lys Leu Lys Asp Val Asn Ala Glu Glu Val Tyr Ser Pro Leu Thr Thr
                100                 105                 110

Pro Val Phe Gly Ser Asp Val Val Tyr Asp Cys Pro Asn Ser Lys Leu
            115                 120                 125

Met Glu Gln Lys Lys Phe Ile Lys Tyr Xaa Leu Thr Gln Ser Ala Leu
130                 135                 140

Glu Ser His Val Pro Leu Ile Glu Lys Glu Val Leu Asp Tyr Leu Arg
145                 150                 155                 160

Asp Ser Pro Asn Phe Gln Gly Ser Ser Gly Arg Met Asp Ile Ser Ala
                165                 170                 175

Ala Met Ala Glu Ile Thr Ile Phe Thr Ala Ala Arg Ala Leu Gln Gly
            180                 185                 190

Gln Glu Val Arg Ser Lys Leu Thr Ala Glu Phe Ala Asp Leu Tyr His
        195                 200                 205

Asp Leu Asp Lys Gly Phe Thr Pro Ile Asn Phe Met Leu Pro Trp Ala
210                 215                 220

Pro Leu Pro His Asn Lys Lys Arg Asp Ala Ala His Ala Arg Met Arg
225                 230                 235                 240

Ser Ile Tyr Val Asp Ile Ile Asn Gln Arg Arg Leu Asp Gly Asp Lys
                245                 250                 255

Asp Ser Gln Lys Ser Asp Met Ile Trp Asn Leu Met Asn Cys Thr Tyr
            260                 265                 270

Lys Asn Gly Gln Gln Val Pro Asp Lys Glu Ile Ala His Met Met Ile
        275                 280                 285

Thr Leu Leu Met Ala Gly Gln His Ser Ser Ser Ile Ser Ala Trp
290                 295                 300

Ile Met Leu Arg Leu Ala Ser Gln Pro Lys Val Leu Glu Glu Leu Tyr
305                 310                 315                 320

Gln Glu Gln Leu Ala Asn Leu Gly Pro Ala Gly Pro Asp Gly Ser Leu
                325                 330                 335

Pro Pro Leu Gln Tyr Lys Asp Leu Asp Lys Leu Pro Phe His Gln His
            340                 345                 350

Val Ile Arg Glu Thr Leu Arg Ile His Ser Ser Ile His Ser Ile Met
        355                 360                 365

Arg Lys Val Lys Ser Pro Leu Pro Val Pro Gly Thr Pro Tyr Met Ile
370                 375                 380

Pro Pro Gly Arg Val Leu Leu Ala Ser Pro Gly Val Thr Ala Leu Ser
385                 390                 395                 400

Asp Glu His Phe Pro Asn Ala Gly Cys Trp Asp Pro His Arg Trp Glu
                405                 410                 415

Asn Gln Ala Thr Lys Glu Gln Glu Asn Asp Glu Val Val Asp Tyr Gly
            420                 425                 430

Tyr Gly Ala Val Ser Lys Gly Thr Ser Ser Pro Tyr Leu Pro Phe Gly
        435                 440                 445

Ala Gly Arg His Arg Cys Ile Gly Glu Lys Phe Ala Tyr Val Asn Leu
450                 455                 460

Gly Val Ile Leu Ala Thr Ile Val Arg His Leu Arg Leu Phe Asn Val
465                 470                 475                 480

Asp Gly Lys Lys Gly Val Pro Glu Thr Asp Tyr Ser Ser Leu Phe Ser
                485                 490                 495

Gly Pro Met Lys Pro Ser Ile Ile Gly Trp Glu Lys Arg Ser Lys Asn
            500                 505                 510
```

Thr Ser Lys
        515

<210> SEQ ID NO 4
<211> LENGTH: 515
<212> TYPE: PRT
<213> ORGANISM: Aspergillus fumigatus
<220> FEATURE:
<221> NAME/KEY: misc_feature
<222> LOCATION: (220)..(220)
<223> OTHER INFORMATION: Xaa can be any naturally occurring amino acid

<400> SEQUENCE: 4

Met Val Pro Met Leu Trp Leu Thr Ala Tyr Met Ala Val Ala Val Leu
1               5                   10                  15

Thr Ala Ile Leu Leu Asn Val Val Tyr Gln Leu Phe Phe Arg Leu Trp
            20                  25                  30

Asn Arg Thr Glu Pro Pro Met Val Phe His Trp Val Pro Phe Leu Gly
        35                  40                  45

Ser Thr Ile Ser Tyr Gly Ile Asp Pro Tyr Lys Phe Phe Ala Cys
    50                  55                  60

Arg Glu Lys Tyr Gly Asp Ile Phe Thr Phe Ile Leu Leu Gly Gln Lys
65                  70                  75                  80

Thr Thr Val Tyr Leu Gly Val Gln Gly Asn Glu Phe Ile Leu Asn Gly
                85                  90                  95

Lys Leu Lys Asp Val Asn Ala Glu Glu Val Tyr Ser Pro Leu Thr Thr
            100                 105                 110

Pro Val Phe Gly Ser Asp Val Val Tyr Asp Cys Pro Asn Ser Lys Leu
        115                 120                 125

Met Glu Gln Lys Lys Phe Ile Lys Tyr Gly Leu Thr Gln Ser Ala Leu
    130                 135                 140

Glu Ser His Val Pro Leu Ile Glu Lys Glu Val Leu Asp Tyr Leu Arg
145                 150                 155                 160

Asp Ser Pro Asn Phe Gln Gly Ser Ser Gly Arg Met Asp Ile Ser Ala
                165                 170                 175

Ala Met Ala Glu Ile Thr Ile Phe Thr Ala Ala Arg Ala Leu Gln Gly
            180                 185                 190

Gln Glu Val Arg Ser Lys Leu Thr Ala Glu Phe Ala Asp Leu Tyr His
        195                 200                 205

Asp Leu Asp Lys Gly Phe Thr Pro Ile Asn Phe Xaa Leu Pro Trp Ala
    210                 215                 220

Pro Leu Pro His Asn Lys Lys Arg Asp Ala Ala His Ala Arg Met Arg
225                 230                 235                 240

Ser Ile Tyr Val Asp Ile Ile Asn Gln Arg Arg Leu Asp Gly Asp Lys
                245                 250                 255

Asp Ser Gln Lys Ser Asp Met Ile Trp Asn Leu Met Asn Cys Thr Tyr
            260                 265                 270

Lys Asn Gly Gln Gln Val Pro Asp Lys Glu Ile Ala His Met Met Ile
        275                 280                 285

Thr Leu Leu Met Ala Gly Gln His Ser Ser Ser Ile Ser Ala Trp
    290                 295                 300

Ile Met Leu Arg Leu Ala Ser Gln Pro Lys Val Leu Glu Glu Leu Tyr
305                 310                 315                 320

Gln Glu Gln Leu Ala Asn Leu Gly Pro Ala Gly Pro Asp Gly Ser Leu
                325                 330                 335

Pro Pro Leu Gln Tyr Lys Asp Leu Asp Lys Leu Pro Phe His Gln His

```
                340                 345                 350
Val Ile Arg Glu Thr Leu Arg Ile His Ser Ser Ile His Ser Ile Met
            355                 360                 365

Arg Lys Val Lys Ser Pro Leu Pro Val Pro Gly Thr Pro Tyr Met Ile
        370                 375                 380

Pro Pro Gly Arg Val Leu Leu Ala Ser Pro Gly Val Thr Ala Leu Ser
385                 390                 395                 400

Asp Glu His Phe Pro Asn Ala Gly Cys Trp Asp Pro His Arg Trp Glu
                405                 410                 415

Asn Gln Ala Thr Lys Glu Gln Glu Asn Asp Glu Val Val Asp Tyr Gly
            420                 425                 430

Tyr Gly Ala Val Ser Lys Gly Thr Ser Ser Pro Tyr Leu Pro Phe Gly
        435                 440                 445

Ala Gly Arg His Arg Cys Ile Gly Glu Lys Phe Ala Tyr Val Asn Leu
    450                 455                 460

Gly Val Ile Leu Ala Thr Ile Val Arg His Leu Arg Leu Phe Asn Val
465                 470                 475                 480

Asp Gly Lys Lys Gly Val Pro Glu Thr Asp Tyr Ser Ser Leu Phe Ser
                485                 490                 495

Gly Pro Met Lys Pro Ser Ile Ile Gly Trp Glu Lys Arg Ser Lys Asn
            500                 505                 510

Thr Ser Lys
        515

<210> SEQ ID NO 5
<211> LENGTH: 515
<212> TYPE: PRT
<213> ORGANISM: Aspergillus fumigatus
<220> FEATURE:
<221> NAME/KEY: misc_feature
<222> LOCATION: (448)..(448)
<223> OTHER INFORMATION: Xaa can be any naturally occurring amino acid

<400> SEQUENCE: 5

Met Val Pro Met Leu Trp Leu Thr Ala Tyr Met Ala Val Ala Val Leu
1               5                   10                  15

Thr Ala Ile Leu Leu Asn Val Val Tyr Gln Leu Phe Phe Arg Leu Trp
            20                  25                  30

Asn Arg Thr Glu Pro Pro Met Val Phe His Trp Val Pro Phe Leu Gly
        35                  40                  45

Ser Thr Ile Ser Tyr Gly Ile Asp Pro Tyr Lys Phe Phe Ala Cys
    50                  55                  60

Arg Glu Lys Tyr Gly Asp Ile Phe Thr Phe Ile Leu Leu Gly Gln Lys
65                  70                  75                  80

Thr Thr Val Tyr Leu Gly Val Gln Gly Asn Glu Phe Ile Leu Asn Gly
            85                  90                  95

Lys Leu Lys Asp Val Asn Ala Glu Glu Val Tyr Ser Pro Leu Thr Thr
            100                 105                 110

Pro Val Phe Gly Ser Asp Val Val Tyr Asp Cys Pro Asn Ser Lys Leu
        115                 120                 125

Met Glu Gln Lys Lys Phe Ile Lys Tyr Gly Leu Thr Gln Ser Ala Leu
130                 135                 140

Glu Ser His Val Pro Leu Ile Glu Lys Glu Val Leu Asp Tyr Leu Arg
145                 150                 155                 160

Asp Ser Pro Asn Phe Gln Gly Ser Ser Gly Arg Met Asp Ile Ser Ala
                165                 170                 175
```

Ala Met Ala Glu Ile Thr Ile Phe Thr Ala Ala Arg Ala Leu Gln Gly
            180                 185                 190

Gln Glu Val Arg Ser Lys Leu Thr Ala Glu Phe Ala Asp Leu Tyr His
            195                 200                 205

Asp Leu Asp Lys Gly Phe Thr Pro Ile Asn Phe Met Leu Pro Trp Ala
            210                 215                 220

Pro Leu Pro His Asn Lys Lys Arg Asp Ala Ala His Ala Arg Met Arg
225                 230                 235                 240

Ser Ile Tyr Val Asp Ile Ile Asn Gln Arg Arg Leu Asp Gly Asp Lys
                245                 250                 255

Asp Ser Gln Lys Ser Asp Met Ile Trp Asn Leu Met Asn Cys Thr Tyr
            260                 265                 270

Lys Asn Gly Gln Gln Val Pro Asp Lys Glu Ile Ala His Met Met Ile
            275                 280                 285

Thr Leu Leu Met Ala Gly Gln His Ser Ser Ser Ile Ser Ala Trp
            290                 295                 300

Ile Met Leu Arg Leu Ala Ser Gln Pro Lys Val Leu Glu Glu Leu Tyr
305                 310                 315                 320

Gln Glu Gln Leu Ala Asn Leu Gly Pro Ala Gly Pro Asp Gly Ser Leu
            325                 330                 335

Pro Pro Leu Gln Tyr Lys Asp Leu Asp Lys Leu Pro Phe His Gln His
            340                 345                 350

Val Ile Arg Glu Thr Leu Arg Ile His Ser Ser Ile His Ser Ile Met
            355                 360                 365

Arg Lys Val Lys Ser Pro Leu Pro Val Pro Gly Thr Pro Tyr Met Ile
            370                 375                 380

Pro Pro Gly Arg Val Leu Leu Ala Ser Pro Gly Val Thr Ala Leu Ser
385                 390                 395                 400

Asp Glu His Phe Pro Asn Ala Gly Cys Trp Asp Pro His Arg Trp Glu
            405                 410                 415

Asn Gln Ala Thr Lys Glu Gln Glu Asn Asp Glu Val Val Asp Tyr Gly
            420                 425                 430

Tyr Gly Ala Val Ser Lys Gly Thr Ser Ser Pro Tyr Leu Pro Phe Xaa
            435                 440                 445

Ala Gly Arg His Arg Cys Ile Gly Glu Lys Phe Ala Tyr Val Asn Leu
            450                 455                 460

Gly Val Ile Leu Ala Thr Ile Val Arg His Leu Arg Leu Phe Asn Val
465                 470                 475                 480

Asp Gly Lys Lys Gly Val Pro Glu Thr Asp Tyr Ser Ser Leu Phe Ser
            485                 490                 495

Gly Pro Met Lys Pro Ser Ile Ile Gly Trp Glu Lys Arg Ser Lys Asn
            500                 505                 510

Thr Ser Lys
      515

<210> SEQ ID NO 6
<211> LENGTH: 2048
<212> TYPE: DNA
<213> ORGANISM: Aspergillus fumigatus
<220> FEATURE:
<221> NAME/KEY: Intron
<222> LOCATION: (554)..(624)

<400> SEQUENCE: 6
ataatcgcag caccacttca gagttgtcta gaatcacgcg gtccggatgt gtgctgagcc    60

```
gaatgaaagt tgcctaatta ctaaggtgta gttccagcat accatacacc ctaactcata      120
ctacggtagg tagatctact tacctatgaa cctatattgg taggtaggtg aatataaaat      180
acagcatgga acatgttttt cattagctgg tctctcattc gtccttgtcc taggccttaa      240
ggaatccagt atatgaaata atccctctta tccatttttcc tcctattctt tttcatttcc     300
ctcatcactg caactctaat cctcgggctc accctccctg tgtctcctcg aaatggtgcc      360
gatgctatgg cttacggcct acatggccgt tgcggtgctg acggcaatct tgctcaatgt      420
tgtttatcaa ttattctttc ggctttggaa ccgaacagaa ccgccaatgg tctttcattg      480
ggtcccattt ctgggtagta ccatcagtta cgggattgat ccctacaagt tcttctttgc      540
gtgcagagaa aaggcaagtc tcaagattgt agtttgacat tcattcctgg gcgcattgct      600
gagtattgct ttcttaaccg gcagtatggc gatatcttca cttttatact gttgggtcaa      660
aaaaccacag tctacctggg cgttcagggg aacgagttta ttctcaacgg caagctcaag      720
gatgtcaatg cggaagaggt ctatagtcca ttgacgaccc ccgttttcgg atcggacgtg      780
gtgtatgatt gtcccaattc caagctgatg gagcagaaaa agttcatcaa gtacggcttg      840
actcagtctg cgttagagtc tcatgtgcca cttattgaga aggaggtttt ggactatctg      900
cgcgattcac cgaactttca aggctcgtcc ggccggatgg acatctctgc ggcaatggct      960
gagattacca ttttttaccgc tgctcgagcc ctccaaggcc aggaagttcg ttccaaactc     1020
acggctgagt tcgctgacct ctatcatgac ctggacaagg gctttactcc catcaatttt     1080
atgctaccgt gggcccccatt gccgcataac aagaagcgag atgctgctca tgcgcgcatg     1140
aggtcaatct acgttgacat catcaatcag cgccgtcttg acggtgacaa ggactctcag     1200
aaatcagaca tgatatggaa cctgatgaac tgcacataca aaaacggcca gcaagtgcct     1260
gataaagaga ttgcgcacat gatgataacc ctgttgatgg ctggtcagca ttcgtcttcg     1320
tccatcagcg cctggattat gctgagactg gcctcacagc caaaagtcct cgaagagctg     1380
tatcaggaac agctggccaa tcttggcccc gccgggccag acggcagtct tcctccgctc     1440
cagtacaagg atcttgacaa acttcccttc catcaacatg ttattcgtga accttacgg      1500 attcactcct ctattcactc tatcatgcgc aaggtgaaaa gccccttgcc cgttcccggg     1560
accccttaca tgattcctcc cggtcgcgtg ctccttgctt cacctggagt gacagccctc     1620
agcgacgaac acttccccaa tgctgggtgc tgggatcccc atcgctggga gaaccaggct     1680
actaaggagc aggagaacga cgaggttgtc gactacggtt acggcgccgt ctccaagggc     1740
acgtcaagtc cctatcttcc gtttggtgct ggccgacacc gctgtatcgg cgagaaattc     1800
gcttatgtca accttggtgt gattctggcg accattgtgc gccacctgcg acttttcaac     1860
gtggatggaa agaaaggagt ccctgaaact gactattcat ccctcttttc gggccccatg     1920
aagccaagca tcatcggctg ggagaagcgg tcgaaaaaca catccaagtg agactgttgt     1980
aaccatcgag gacttcaaag gatttggtgt gatcggaata ggtgtattat acttaattca     2040
cccctcga                                                              2048
```

<210> SEQ ID NO 7
<211> LENGTH: 2048
<212> TYPE: DNA
<213> ORGANISM: Aspergillus fumigatus
<220> FEATURE:
<221> NAME/KEY: Intron
<222> LOCATION: (1425)..(1495)

<400> SEQUENCE: 7

```
tcgagggtg aattaagtat aatacaccta ttccgatcac accaaatcct ttgaagtcct      60
cgatggttac aacagtctca cttggatgtg tttttcgacc gcttctccca gccgatgatg     120
cttggcttca tggggcccga aaagagggat gaatagtcag tttcagggac tcctttcttt    180
ccatccacgt tgaaaagtcg caggtggcgc acaatggtcg ccagaatcac accaaggttg    240
acataagcga atttctcgcc gatacagcgg tgtcggccag caccaaacgg aagatagga     300 cttgacgtgc ccttggagac ggcgccgtaa ccgtagtcga caacctcgtc gttctcctgc    360
tccttagtag cctggttctc ccagcgatgg ggatcccagc acccagcatt ggggaagtgt    420
tcgtcgctga gggctgtcac tccaggtgaa gcaaggagca cgcgaccggg aggaatcatg    480 taagggtcc cgggaacggg caaggggctt ttcaccttgc gcatgataga gtgaatagag     540
gagtgaatcc gtaaggtttc acgaataaca tgttgatgga agggaagttt gtcaagatcc    600
ttgtactgga gcggaggaag actgccgtct ggcccggcgg ggccaagatt ggccagctgt    660
tcctgataca gctcttcgag gacttttggc tgtgaggcca gtctcagcat aatccaggcg    720
ctgatggacg aagacgaatg ctgaccagcc atcaacaggg ttatcatcat gtgcgcaatc    780
tctttatcag gcacttgctg gccgtttttg tatgtgcagt tcatcaggtt ccatatcatg    840
tctgatttct gagagtcctt gtcaccgtca agacggcgct gattgatgat gtcaacgtag    900
attgacctca tgcgcgcatg agcagcatct cgcttcttgt tatgcggcaa tgggcccac    960 ggtagcataa aattgatggg agtaaagccc ttgtccaggt catgatagag gtcagcgaac   1020
tcagccgtga gtttggaacg aacttcctgg ccttggaggg ctcgagcagc ggtaaaaatg   1080
gtaatctcag ccattgccgc agagatgtcc atccggccgg acgagccttg aaagttcggt   1140
gaatcgcgca gatagtccaa aacctccttc tcaataagtg gcacatgaga ctctaacgca   1200
gactgagtca agccgtactt gatgaacttt ttctgctcca tcagcttgga attgggacaa   1260
tcatacacca cgtccgatcc gaaaacgggg tcgtcaatg gactatagac ctcttccgca    1320
ttgacatcct tgagcttgcc gttgagaata aactcgttcc cctgaacgcc caggtagact   1380 gtggttttt gacccaacag tataaaagtg aagtatcgc catactgccg gttaagaaag    1440
caatactcag caatgcgccc aggaatgaat gtcaaactac aatcttgaga cttgcctttt   1500
ctctgcacgc aaagaagaac ttgtagggat caatcccgta actgatggta ctacccagaa   1560
atgggaccca atgaaagacc attggcggtt ctgttcggtt ccaaagccga aagaataatt   1620
gataaacaac attgagcaag attgccgtca gcaccgcaac ggccatgtag gccgtaagcc   1680
atagcatcgg caccatttcg aggagacaca gggagggtga gcccgaggat tagagttgca   1740
gtgatgaggg aaatgaaaaa gaataggagg aaaatggata agagggatta tttcatatac   1800
tggattcctt aaggcctagg acaaggacga atgagagacc agctaatgaa aaacatgttc   1860
catgctgtat tttatattca cctacctacc aatataggtt cataggtaag tagatctacc   1920
taccgtagta tgagttaggg tgtatggtat gctggaacta caccttagta attaggcaac   1980
tttcattcgg ctcagcacac atccggaccg cgtgattcta gacaactctg aagtggtgct   2040
gcgattat                                                            2048
```

<210> SEQ ID NO 8
<211> LENGTH: 2048
<212> TYPE: DNA
<213> ORGANISM: Aspergillus fumigatus
<220> FEATURE:
<221> NAME/KEY: misc_feature
<222> LOCATION: (512)..(513)

<223> OTHER INFORMATION: n is a, c, g, or t
<220> FEATURE:
<221> NAME/KEY: Intron
<222> LOCATION: (554)..(624)

<400> SEQUENCE: 8

```
ataatcgcag caccacttca gagttgtcta gaatcacgcg gtccggatgt gtgctgagcc      60
gaatgaaagt tgcctaatta ctaaggtgta gttccagcat accatacacc ctaactcata     120
ctacggtagg tagatctact tacctatgaa cctatattgg taggtaggtg aatataaaat     180
acagcatgga acatgttttt cattagctgg tctctcattc gtccttgtcc taggccttaa     240
ggaatccagt atatgaaata atccctctta tccattttcc tcctattctt tttcatttcc     300
ctcatcactg caactctaat cctcgggctc accctccctg tgtctcctcg aaatggtgcc     360
gatgctatgg cttacggcct acatggccgt tgcggtgctg acggcaatct tgctcaatgt     420
tgtttatcaa ttattctttc ggctttggaa ccgaacagaa ccgccaatgg tctttcattg     480
ggtcccattt ctgggtagta ccatcagtta cnngattgat ccctacaagt tcttctttgc     540
gtgcagagaa aaggcaagtc tcaagattgt agtttgacat tcattcctgg gcgcattgct     600
gagtattgct ttcttaaccg gcagtatggc gatatcttca cttttatact gttgggtcaa     660
aaaaccacag tctacctggg cgttcagggg aacgagttta ttctcaacgg caagctcaag     720
gatgtcaatg cggaagaggt ctatagtcca ttgacgaccc ccgttttcgg atcggacgtg     780
gtgtatgatt gtcccaattc caagctgatg gagcagaaaa agttcatcaa gtacggcttg     840
actcagtctg cgttagagtc tcatgtgcca cttattgaga aggaggtttt ggactatctg     900
cgcgattcac cgaactttca aggctcgtcc ggccggatgg acatctctgc ggcaatggct     960
gagattacca tttttaccgc tgctcgagcc ctccaaggcc aggaagttcg ttccaaactc    1020
acggctgagt tcgctgacct ctatcatgac ctggacaagg gctttactcc catcaatttt    1080
atgctaccgt gggcccccatt gccgcataac aagaagcgag atgctgctca tgcgcgcatg    1140
aggtcaatct acgttgacat catcaatcag cgccgtcttg acggtgacaa ggactctcag    1200
aaatcagaca tgatatggaa cctgatgaac tgcacataca aaaacggcca gcaagtgcct    1260
gataaagaga ttgcgcacat gatgataacc ctgttgatgg ctggtcagca ttcgtcttcg    1320
tccatcagcg cctggattat gctgagactg gcctcacagc caaaagtcct cgaagagctg    1380
tatcaggaac agctggccaa tcttggcccc gccgggccag acggcagtct tcctccgctc    1440
cagtacaagg atcttgacaa acttcccttc catcaacatg ttattcgtga aaccttacgg    1500
attcactcct ctattcactc tatcatgcgc aaggtgaaaa gccccttgcc cgttcccggg    1560
accccttaca tgattcctcc cggtcgcgtg ctccttgctt cacctggagt gacagccctc    1620
agcgacgaac acttccccaa tgctgggtgc tgggatcccc atcgctggga gaaccaggct    1680
actaaggagc aggagaacga cgaggttgtc gactacggtt acggcgccgt ctccaagggc    1740
acgtcaagtc cctatcttcc gtttggtgct ggccgacacc gctgtatcgg cgagaaattc    1800
gcttatgtca accttggtgt gattctggcg accattgtgc gccacctgcg acttttcaac    1860
gtggatggaa agaaaggagt ccctgaaact gactattcat ccctcttttc gggccccatg    1920
aagccaagca tcatcggctg ggagaagcgg tcgaaaaaca catccaagtg agactgttgt    1980
aaccatcgag gacttcaaag gatttggtgt gatcggaata ggtgtattat acttaattca    2040
ccctctcga                                                             2048
```

<210> SEQ ID NO 9

<211> LENGTH: 2048
<212> TYPE: DNA
<213> ORGANISM: Aspergillus fumigatus
<220> FEATURE:
<221> NAME/KEY: Intron
<222> LOCATION: (1425)..(1495)
<220> FEATURE:
<221> NAME/KEY: misc_feature
<222> LOCATION: (1536)..(1537)
<223> OTHER INFORMATION: n is a, c, g, or t

<400> SEQUENCE: 9

```
tcgagggtg aattaagtat aatacaccta ttccgatcac accaaatcct tgaagtcct      60
cgatggttac aacagtctca cttggatgtg tttttcgacc gcttctccca gccgatgatg    120
cttggcttca tggggcccga aaagagggat gaatagtcag tttcagggac tcctttcttt   180
ccatccacgt tgaaaagtcg caggtggcgc acaatggtcg ccagaatcac accaaggttg   240
acataagcga atttctcgcc gatacagcgg tgtcggccag caccaaacgg aagatagga   300
cttgacgtgc ccttggagac ggcgccgtaa ccgtagtcga caacctcgtc gttctcctgc   360
tccttagtag cctggttctc ccagcgatgg ggatcccagc acccagcatt ggggaagtgt   420
tcgtcgctga gggctgtcac tccaggtgaa gcaaggagca cgcgaccggg aggaatcatg   480
taagggtcc cgggaacggg caaggggctt ttcaccttgc gcatgataga gtgaatagag    540
gagtgaatcc gtaaggtttc acgaataaca tgttgatgga agggaagttt gtcaagatcc   600
ttgtactgga gcggaggaag actgccgtct ggcccggcgg ggccaagatt ggccagctgt   660
tcctgataca gctcttcgag gactttggc tgtgaggcca gtctcagcat aatccaggcg     720
ctgatggacg aagacgaatg ctgaccagcc atcaacaggg ttatcatcat gtgcgcaatc   780
tctttatcag gcacttgctg gccgtttttg tatgtgcagt tcatcaggtt ccatatcatg   840
tctgatttct gagagtcctt gtcaccgtca agacggcgct gattgatgat gtcaacgtag   900
attgacctca tgcgcgcatg agcagcatct cgcttcttgt tatgcggcaa tggggcccac   960
ggtagcataa aattgatggg agtaaagccc ttgtccaggt catgatagag gtcagcgaac  1020
tcagccgtga gtttggaacg aacttcctgg ccttggaggg ctcgagcagc ggtaaaaatg  1080
gtaatctcag ccattgccgc agagatgtcc atccggccgg acgagccttg aaagttcggt  1140
gaatcgcgca gatagtccaa aacctccttc tcaataagtg gcacatgaga ctctaacgca  1200
gactgagtca agccgtactt gatgaacttt ttctgctcca tcagcttgga attgggacaa  1260
tcatacacca cgtccgatcc gaaaacgggg gtcgtcaatg gactatagac ctcttccgca  1320
ttgacatcct tgagcttgcc gttgagaata aactcgttcc cctgaacgcc caggtagact  1380
gtggttttt gacccaacag tataaaagtg aagatatcgc catactgccg gttaagaaag   1440
caatactcag caatgcgccc aggaatgaat gtcaaactac aatcttgaga cttgcctttt  1500
ctctgcacgc aaagaagaac ttgtagggat caatcnngta actgatggta ctacccagaa  1560
atgggaccca atgaaagacc attggcggtt ctgttcggtt ccaaagccga agaataatt   1620
gataaacaac attgagcaag attgccgtca gcaccgcaac ggccatgtag gccgtaagcc  1680
atagcatcgg caccatttcg aggagacaca gggagggtga gcccgaggat tagagttgca  1740
gtgatgaggg aaatgaaaaa gaataggagg aaaatggata gagggatta tttcatatac    1800
tggattcctt aaggcctagg acaaggacga atgagagacc agctaatgaa aaacatgttc  1860
catgctgtat tttatattca cctacctacc aatataggtt cataggtaag tagatctacc   1920
taccgtagta tgagttaggg tgtatggtat gctggaacta caccttagta attaggcaac   1980
```

```
tttcattcgg ctcagcacac atccggaccg cgtgattcta gacaactctg aagtggtgct    2040
gcgattat                                                              2048

<210> SEQ ID NO 10
<211> LENGTH: 2048
<212> TYPE: DNA
<213> ORGANISM: Aspergillus fumigatus
<220> FEATURE:
<221> NAME/KEY: Intron
<222> LOCATION: (554)..(624)
<220> FEATURE:
<221> NAME/KEY: misc_feature
<222> LOCATION: (835)..(836)
<223> OTHER INFORMATION: n is a, c, g, or t

<400> SEQUENCE: 10
ataatcgcag caccacttca gagttgtcta gaatcacgcg gtccggatgt gtgctgagcc      60
gaatgaaagt tgcctaatta ctaaggtgta gttccagcat accatacacc ctaactcata     120
ctacggtagg tagatctact tacctatgaa cctatattgg taggtaggtg aatataaaat     180
acagcatgga acatgttttt cattagctgg tctctcattc gtccttgtcc taggccttaa     240
ggaatccagt atatgaaata atccctctta tccatttttcc tcctattctt tttcatttcc    300
ctcatcactg caactctaat cctcgggctc accctccctg tgtctcctcg aaatggtgcc     360
gatgctatgg cttacggcct acatggccgt tgcggtgctg acggcaatct tgctcaatgt     420
tgtttatcaa ttattctttc ggctttggaa ccgaacagaa ccgccaatgg tctttcattg     480
ggtcccattt ctgggtagta ccatcagtta cgggattgat ccctacaagt tcttctttgc     540
gtgcagagaa aaggcaagtc tcaagattgt agtttgacat tcattcctgg gcgcattgct     600
gagtattgct ttcttaaccg gcagtatggc gatatcttca cttttatact gttgggtcaa     660
aaaaccacag tctacctggg cgttcagggg aacgagttta ttctcaacgg caagctcaag     720
gatgtcaatg cggaagaggt ctatagtcca ttgacgaccc ccgttttcgg atcggacgtg     780
gtgtatgatt gtcccaattc caagctgatg gagcagaaaa agttcatcaa gtacnncttg     840
actcagtctg cgttagagtc tcatgtgcca cttattgaga aggaggtttt ggactatctg     900
cgcgattcac cgaactttca aggctcgtcc ggccggatgg acatctctgc ggcaatggct     960
gagattacca tttttaccgc tgctcgagcc ctccaaggcc aggaagttcg ttccaaactc    1020
acggctgagt tcgctgacct ctatcatgac ctggacaagg gctttactcc catcaatttt    1080
atgctaccgt gggcccccat tgccgcataa caagaagcgag atgctgctca tgcgcgcatg    1140
aggtcaatct acgttgacat catcaatcag cgccgtcttg acggtgacaa ggactctcag    1200
aaatcagaca tgatatggaa cctgatgaac tgcacataca aaaacggcca gcaagtgcct    1260
gataaagaga ttgcgcacat gatgataacc ctgttgatgg ctggtcagca ttcgtcttcg    1320
tccatcagcg cctggattat gctgagactg gcctcacagc caaaagtcct cgaagagctg    1380
tatcaggaac agctggccaa tcttggcccc gcgggccag acggcagtct tcctccgctc    1440
cagtacaagg atcttgacaa acttcccttc catcaacatg ttattcgtga aaccttacgg    1500
attcactcct ctattcactc tatcatgcgc aaggtgaaaa gccccttgcc cgttcccggg    1560
accccttaca tgattcctcc cggtcgcgtg ctccttgctt cacctggagt gacagccctc    1620
agcgacgaac acttccccaa tgctgggtgc tgggatcccc atcgctggga gaaccaggct    1680
actaaggagc aggagaacga cgaggttgtc gactacggtt acggcgccgt ctccaagggc    1740
acgtcaagtc cctatcttcc gtttggtgct ggccgacacc gctgtatcgg cgagaaattc    1800
```

| gcttatgtca acccttggtgt gattctggcg accattgtgc gccacctgcg acttttcaac | 1860 |
| gtggatggaa agaaaggagt ccctgaaact gactattcat ccctcttttc gggccccatg | 1920 |
| aagccaagca tcatcggctg ggagaagcgg tcgaaaaaca catccaagtg agactgttgt | 1980 |
| aaccatcgag gacttcaaag gatttggtgt gatcggaata ggtgtattat acttaattca | 2040 |
| cccctcga | 2048 |

```
<210> SEQ ID NO 11
<211> LENGTH: 2048
<212> TYPE: DNA
<213> ORGANISM: Aspergillus fumigatus
<220> FEATURE:
<221> NAME/KEY: misc_feature
<222> LOCATION: (1213)..(1214)
<223> OTHER INFORMATION: n is a, c, g, or t
<220> FEATURE:
<221> NAME/KEY: Intron
<222> LOCATION: (1425)..(1495)
```

<400> SEQUENCE: 11

| tcgagggtg aattaagtat aatacaccta ttccgatcac accaaatcct tgaagtcct | 60 |
| cgatggttac aacagtctca cttggatgtg ttttcgacc gcttctccca gccgatgatg | 120 |
| cttggcttca tggggcccga aaagagggat gaatagtcag tttcagggac tcctttcttt | 180 |
| ccatccacgt tgaaaagtcg caggtggcgc acaatggtcg ccagaatcac accaaggttg | 240 |
| acataagcga atttctcgcc gatacagcgg tgtcggccag caccaaacgg aagataggga | 300 |
| cttgacgtgc ccttggagac ggcgccgtaa ccgtagtcga caacctcgtc gttctccctgc | 360 |
| tccttagtag cctggttctc ccagcgatgg ggatcccagc acccagcatt ggggaagtgt | 420 |
| tcgtcgctga gggctgtcac tccaggtgaa gcaggagca cgcgaccggg aggaatcatg | 480 |
| taagggggtcc cgggaacggg caaggggctt ttcaccttgc gcatgataga gtgaatagag | 540 |
| gagtgaatcc gtaaggtttc acgaataaca tgttgatgga agggaagttt gtcaagatcc | 600 |
| ttgtactgga gcggaggaag actgccgtct ggcccggcgg ggccaagatt ggccagctgt | 660 |
| tcctgataca gctcttcgag gacttttggc tgtgaggcca gtctcagcat aatccaggcg | 720 |
| ctgatggacg aagacgaatg ctgaccagcc atcaacaggg ttatcatcat gtgcgcaatc | 780 |
| tctttatcag gcacttgctg gccgtttttg tatgtgcagt tcatcaggtt ccatatcatg | 840 |
| tctgatttct gagagtcctt gtcaccgtca agacggcgct gattgatgat gtcaacgtag | 900 |
| attgacctca tgcgcgcatg agcagcatct cgcttcttgt tatgcggcaa tggggcccac | 960 |
| ggtagcataa aattgatggg agtaaagccc ttgtccaggt catgatagag gtcagcgaac | 1020 |
| tcagccgtga gtttggaacg aacttcctgg ccttggaggg ctcgagcagc ggtaaaaatg | 1080 |
| gtaatctcag ccattgccgc agagatgtcc atccggccgg acgagccttg aaagttcggt | 1140 |
| gaatcgcgca gatagtccaa aacctccttc tcaataagtg gcacatgaga ctctaacgca | 1200 |
| gactgagtca agnngtactt gatgaacttt ttctgctcca tcagcttgga attgggacaa | 1260 |
| tcatacacca cgtccgatcc gaaaacgggg gtcgtcaatg gactatagac ctcttccgca | 1320 |
| ttgacatcct tgagcttgcc gttgagaata aactcgttcc cctgaacgcc caggtagact | 1380 |
| gtggttttt gacccaacag tataaaagtg aagatatcgc catactgccg gttaagaaag | 1440 |
| caatactcag caatgcgccc aggaatgaat gtcaaactac aatcttgaga cttgccttt | 1500 |
| ctctgcacgc aaagaagaac ttgtagggat caatcccgta actgatggta ctacccagaa | 1560 |
| atgggaccca atgaaagacc attggcggtt ctgttcggtt ccaaagccga aagaataatt | 1620 |

```
gataaacaac attgagcaag attgccgtca gcaccgcaac ggccatgtag gccgtaagcc      1680
atagcatcgg caccatttcg aggagacaca gggagggtga gcccgaggat tagagttgca      1740
gtgatgaggg aaatgaaaaa gaataggagg aaaatggata agagggatta tttcatatac      1800
tggattcctt aaggcctagg acaaggacga atgagagacc agctaatgaa aaacatgttc      1860
catgctgtat tttatattca cctacctacc aatataggtt cataggtaag tagatctacc      1920
taccgtagta tgagttaggg tgtatggtat gctggaacta caccttagta attaggcaac      1980
tttcattcgg ctcagcacac atccggaccg cgtgattcta gacaactctg aagtggtgct      2040
gcgattat                                                               2048

<210> SEQ ID NO 12
<211> LENGTH: 2048
<212> TYPE: DNA
<213> ORGANISM: Aspergillus fumigatus
<220> FEATURE:
<221> NAME/KEY: Intron
<222> LOCATION: (554)..(624)
<220> FEATURE:
<221> NAME/KEY: misc_feature
<222> LOCATION: (1081)..(1083)
<223> OTHER INFORMATION: n is a, c, g, or t

<400> SEQUENCE: 12
ataatcgcag caccacttca gagttgtcta gaatcacgcg gtccggatgt gtgctgagcc       60
gaatgaaagt tgcctaatta ctaaggtgta gttccagcat accatacacc ctaactcata      120
ctacggtagg tagatctact taccctatgaa cctatattgg taggtaggtg aatataaaat     180
acagcatgga acatgttttt cattagctgg tctctcattc gtccttgtcc taggccttaa      240
ggaatccagt atatgaaata atccctctta tccattttcc tcctattctt tttcatttcc      300
ctcatcactg caactctaat cctcgggctc accctccctg tgtctcctcg aaatggtgcc      360
gatgctatgg cttacggcct acatggccgt tgcggtgctg acggcaatct tgctcaatgt      420
tgtttatcaa ttattctttc ggctttggaa ccgaacagaa ccgccaatgg tctttcattg      480
ggtcccattt ctgggtagta ccatcagtta cgggattgat ccctacaagt tcttctttgc      540
gtgcagagaa aaggcaagtc tcaagattgt agtttgacat tcattcctgg gcgcattgct      600
gagtattgct ttcttaaccg gcagtatggc gatatcttca cttttatact gttgggtcaa      660
aaaaccacag tctacctggg cgttcagggg aacgagttta ttctcaacgg caagctcaag      720
gatgtcaatg cggaagaggt ctatagtcca ttgacgaccc ccgttttcgg atcggacgtg      780
gtgtatgatt gtcccaattc caagctgatg gagcagaaaa agttcatcaa gtacggcttg      840
actcagtctg cgttagagtc tcatgtgcca cttattgaga aggaggtttt ggactatctg      900
cgcgattcac cgaactttca aggctcgtcc ggccggatgg acatctctgc ggcaatggct      960
gagattacca ttttaccgc tgctcgagcc ctccaaggcc aggaagttcg ttccaaactc      1020
acggctgagt cgctgacct ctatcatgac ctggacaagg gctttactcc catcaatttt      1080
nnnctaccgt gggcccatt gccgcataac aagaagcgag atgctgctca tgcgcgcatg      1140
aggtcaatct acgttgacat catcaatcag cgccgtcttg acggtgacaa ggactctcag      1200
aaatcagaca tgatatggaa cctgatgaac tgcacataca aaaacggcca gcaagtgcct      1260
gataaagaga ttgcgcacat gatgataacc ctgttgatgg ctggtcagca ttcgtcttcg      1320
tccatcagcg cctggattat gctgagactg gcctcacagc caaaagtcct cgaagagctg      1380
tatcaggaac agctggccaa tcttggcccc gccgggccag acggcagtct tcctccgctc      1440
```

```
cagtacaagg atcttgacaa acttcccttc catcaacatg ttattcgtga aaccttacgg   1500
attcactcct ctattcactc tatcatgcgc aaggtgaaaa gcccttgcc cgttcccggg    1560 accccttaca tgattcctcc cggtcgcgtg ctccttgctt cacctggagt gacagccctc   1620
agcgacgaac acttccccaa tgctgggtgc tgggatcccc atcgctggga gaaccaggct   1680
actaaggagc aggagaacga cgaggttgtc gactacggtt acggcgccgt ctccaagggc   1740
acgtcaagtc cctatcttcc gtttggtgct ggccgacacc gctgtatcgg cgagaaattc   1800
gcttatgtca accttggtgt gattctggcg accattgtgc gccacctgcg acttttcaac   1860
gtggatggaa agaaaggagt ccctgaaact gactattcat ccctcttttc gggccccatg   1920
aagccaagca tcatcggctg ggagaagcgg tcgaaaaaca catccaagtg agactgttgt   1980
aaccatcgag gacttcaaag gatttggtgt gatcggaata ggtgtattat acttaattca   2040
cccctcga                                                           2048
```

<210> SEQ ID NO 13
<211> LENGTH: 2048
<212> TYPE: DNA
<213> ORGANISM: Aspergillus fumigatus
<220> FEATURE:
<221> NAME/KEY: misc_feature
<222> LOCATION: (966)..(968)
<223> OTHER INFORMATION: n is a, c, g, or t
<220> FEATURE:
<221> NAME/KEY: Intron
<222> LOCATION: (1425)..(1495)

<400> SEQUENCE: 13

```
tcgagggtg aattaagtat aatacaccta ttccgatcac accaaatcct ttgaagtcct     60
cgatggttac aacagtctca cttggatgtg tttttcgacc gcttctccca gccgatgatg   120
cttggcttca tggggcccga aaagagggat gaatagtcag tttcagggac tcctttcttt   180
ccatccacgt tgaaaagtcg caggtggcgc acaatggtcg ccagaatcac accaaggttg   240
acataagcga atttctcgcc gatacagcgg tgtcggccag caccaaacgg aagatagggga  300 cttgacgtgc ccttggagac ggcgccgtaa ccgtagtcga caacctcgtc gttctcctgc   360
tccttagtag cctggttctc ccagcgatgg ggatcccagc acccagcatt ggggaagtgt   420
tcgtcgctga gggctgtcac tccaggtgaa gcaaggagca cgcgaccggg aggaatcatg   480
taaggggtcc cgggaacggg caaggggctt ttcaccttgc gcatgataga gtgaatagag   540
gagtgaatcc gtaaggtttc acgaataaca tgttgatgga agggaagttt gtcaagatcc   600
ttgtactgga gcggaggaag actgccgtct ggcccggcgg ggccaagatt ggccagctgt   660
tcctgataca gctcttcgag acttttggc tgtgaggcca gtctcagcat aatccaggcg    720
ctgatggacg aagacgaatg ctgaccagcc atcaacaggg ttatcatcat gtgcgcaatc   780
tctttatcag gcacttgctg gccgtttttg tatgtgcagt tcatcaggtt ccatatcatg   840
tctgatttct gagagtcctt gtcaccgtca agacggcgct gattgatgat gtcaacgtag   900
attgacctca tgcgcgcatg agcagcatct cgcttcttgt tatgcggcaa tggggcccac   960
ggtagnnnaa aattgatggg agtaaagccc ttgtccaggt catgatagag gtcagcgaac  1020
tcagccgtga gtttggaacg aacttcctgg ccttggaggg ctcgagcagc ggtaaaatg   1080 gtaatctcag ccattgccgc agagatgtcc atccggccgg acgagccttg aaagttcggt  1140
gaatcgcgca gatagtccaa aacctccttc tcaataagtg gcacatgaga ctctaacgca  1200
gactgagtca agccgtactt gatgaacttt ttctgctcca tcagcttgga attgggacaa  1260
```

```
tcatacacca cgtccgatcc gaaaacgggg gtcgtcaatg gactatagac ctcttccgca   1320
ttgacatcct tgagcttgcc gttgagaata aactcgttcc cctgaacgcc caggtagact   1380
gtggtttttt gacccaacag tataaaagtg aagatatcgc catactgccg gttaagaaag   1440
caatactcag caatgcgccc aggaatgaat gtcaaactac aatcttgaga cttgcctttt   1500
ctctgcacgc aaagaagaac ttgtagggat caatcccgta actgatggta ctacccagaa   1560
atgggaccca atgaaagacc attggcggtt ctgttcggtt ccaaagccga agaataatt    1620 gataaacaac attgagcaag attgccgtca gcaccgcaac ggccatgtag gccgtaagcc   1680
atagcatcgg caccatttcg aggagacaca gggagggtga gcccgaggat tagagttgca   1740
gtgatgaggg aaatgaaaaa gaataggagg aaaatggata agagggatta tttcatatac   1800
tggattcctt aaggcctagg acaaggacga atgagagacc agctaatgaa aaacatgttc   1860
catgctgtat tttatattca cctacctacc aatataggtt cataggtaag tagatctacc   1920
taccgtagta tgagttaggg tgtatggtat gctggaacta caccttagta attaggcaac   1980
tttcattcgg ctcagcacac atccggaccg cgtgattcta gacaactctg aagtggtgct   2040
gcgattat                                                           2048

<210> SEQ ID NO 14
<211> LENGTH: 2048
<212> TYPE: DNA
<213> ORGANISM: Aspergillus fumigatus
<220> FEATURE:
<221> NAME/KEY: Intron
<222> LOCATION: (554)..(624)
<220> FEATURE:
<221> NAME/KEY: misc_feature
<222> LOCATION: (1765)..(1766)
<223> OTHER INFORMATION: n is a, c, g, or t

<400> SEQUENCE: 14
ataatcgcag caccacttca gagttgtcta gaatcacgcg gtccggatgt gtgctgagcc     60
gaatgaaagt tgcctaatta ctaaggtgta gttccagcat accatacacc ctaactcata    120
ctacggtagg tagatctact tacctatgaa cctatattgg taggtaggtg aatataaaat    180
acagcatgga acatgttttt cattagctgg tctctcattc gtccttgtcc taggccttaa    240
ggaatccagt atatgaaata atccctctta tccatttcc tcctattctt tttcatttcc    300
ctcatcactg caactctaat cctcgggctc accctccctg tgtctcctcg aaatggtgcc    360
gatgctatgg cttacggcct acatggccgt tgcggtgctg acggcaatct tgctcaatgt    420
tgtttatcaa ttattcttc ggctttggaa ccgaacagaa ccgccaatgg tctttcattg     480
ggtcccattt ctgggtagta ccatcagtta cgggattgat ccctacaagt tcttctttgc    540
gtgcagagaa aaggcaagtc tcaagattgt agtttgacat tcattcctgg gcgcattgct    600
gagtattgct ttcttaaccg gcagtatggc gatatcttca cttttatact gttgggtcaa    660
aaaaccacag tctacctggg cgttcagggg aacgagttta ttctcaacgg caagctcaag   720
gatgtcaatg cggaagaggt ctatagtcca ttgacgaccc ccgttttcgg atcggacgtg    780
gtgtatgatt gtcccaattc caagctgatg gagcagaaaa agttcatcaa gtacggcttg    840
actcagtctg cgttagagtc tcatgtgcca cttattgaga aggaggtttt ggactatctg    900
cgcgattcac cgaactttca aggctcgtcc ggccggatgg acatctctgc ggcaatggct    960
gagattacca ttttaccgc tgctcgagcc ctccaaggcc aggaagttcg ttccaaactc    1020
acggctgagt tcgctgacct ctatcatgac ctggacaagg gctttactcc catcaatttt   1080
```

-continued

| | |
|---|---|
| atgctaccgt gggcccatt gccgcataac aagaagcgag atgctgctca tgcgcgcatg | 1140 |
| aggtcaatct acgttgacat catcaatcag cgccgtcttg acggtgacaa ggactctcag | 1200 |
| aaatcagaca tgatatggaa cctgatgaac tgcacataca aaaacggcca gcaagtgcct | 1260 |
| gataaagaga ttgcgcacat gatgataacc ctgttgatgg ctggtcagca ttcgtcttcg | 1320 |
| tccatcagcg cctggattat gctgagactg gcctcacagc caaaagtcct cgaagagctg | 1380 |
| tatcaggaac agctggccaa tcttggcccc gccgggccag acggcagtct tcctccgctc | 1440 |
| cagtacaagg atcttgacaa acttcccttc catcaacatg ttattcgtga aaccttacgg | 1500 |
| attcactcct ctattcactc tatcatgcgc aaggtgaaaa gccccttgcc cgttcccggg | 1560 |
| accccttaca tgattcctcc cggtcgcgtg ctccttgctt cacctggagt gacagccctc | 1620 |
| agcgacgaac acttccccaa tgctgggtgc tgggatcccc atcgctggga gaaccaggct | 1680 |
| actaaggagc aggagaacga cgaggttgtc gactacggtt acggcgccgt ctccaagggc | 1740 |
| acgtcaagtc cctatcttcc gtttnntgct ggccgacacc gctgtatcgg cgagaaattc | 1800 |
| gcttatgtca accttggtgt gattctggcg accattgtgc gccacctgcg acttttcaac | 1860 |
| gtggatggaa agaaaggagt ccctgaaact gactattcat ccctcttttc gggccccatg | 1920 |
| aagccaagca tcatcggctg ggagaagcgg tcgaaaaaca catccaagtg agactgttgt | 1980 |
| aaccatcgag gacttcaaag gatttggtgt gatcggaata ggtgtattat acttaattca | 2040 |
| cccctcga | 2048 |

<210> SEQ ID NO 15
<211> LENGTH: 2048
<212> TYPE: DNA
<213> ORGANISM: Aspergillus fumigatus
<220> FEATURE:
<221> NAME/KEY: misc_feature
<222> LOCATION: (283)..(284)
<223> OTHER INFORMATION: n is a, c, g, or t
<220> FEATURE:
<221> NAME/KEY: Intron
<222> LOCATION: (1425)..(1495)

<400> SEQUENCE: 15

| | |
|---|---|
| tcgagggtg aattaagtat aatacaccta ttccgatcac accaaatcct ttgaagtcct | 60 |
| cgatggttac aacagtctca cttggatgtg ttttcgacc gcttctccca gccgatgatg | 120 |
| cttggcttca tggggcccga aaagagggat gaatagtcag tttcagggac tccttcttt | 180 |
| ccatccacgt tgaaaagtcg caggtggcgc acaatggtcg ccagaatcac accaaggttg | 240 |
| acataagcga atttctcgcc gatacagcgg tgtcggccag cannaaacgg aagataggga | 300 |
| cttgacgtgc ccttggagac ggcgccgtaa ccgtagtcga caacctcgtc gttctcctgc | 360 |
| tccttagtag cctggttctc ccagcgatgg ggatcccagc acccagcatt ggggaagtgt | 420 |
| tcgtcgctga gggctgtcac tccaggtgaa gcaaggagca cgcgaccggg aggaatcatg | 480 |
| taagggtcc cgggaacggg caaggggctt ttcaccttgc gcatgataga gtgaatagag | 540 |
| gagtgaatcc gtaaggtttc acgaataaca tgttgatgga agggaagttt gtcaagatcc | 600 |
| ttgtactgga gcgaggaag actgccgtct ggcccggcgg ggccaagatt ggccagctgt | 660 |
| tcctgataca gctcttcgag actttggc tgtgaggcca gtctcagcat aatccaggcg | 720 |
| ctgatggacg aagacgaatg ctgaccagcc atcaacaggg ttatcatcat gtgcgcaatc | 780 |
| tctttatcag gcacttgctg gccgttttg tatgtgcagt tcatcaggtt ccatatcatg | 840 |
| tctgatttct gagagtcctt gtcaccgtca agacggcgct gattgatgat gtcaacgtag | 900 |

-continued

```
attgacctca tgcgcgcatg agcagcatct cgcttcttgt tatgcggcaa tggggcccac      960
ggtagcataa aattgatggg agtaaagccc ttgtccaggt catgatagag gtcagcgaac     1020
tcagccgtga gtttggaacg aacttcctgg ccttggaggg ctcgagcagc ggtaaaaatg     1080
gtaatctcag ccattgccgc agagatgtcc atccggccgg acgagccttg aaagttcggt     1140
gaatcgcgca gatagtccaa aacctccttc tcaataagtg gcacatgaga ctctaacgca     1200
gactgagtca agccgtactt gatgaacttt ttctgctcca tcagcttgga attgggacaa     1260
tcatacacca cgtccgatcc gaaaacgggg gtcgtcaatg gactatagac ctcttccgca     1320
ttgacatcct tgagcttgcc gttgagaata aactcgttcc cctgaacgcc caggtagact     1380 gtggttttt gacccaacag tataaaagtg aagatatcgc catactgccg gttaagaaag      1440
caatactcag caatgcgccc aggaatgaat gtcaaactac aatcttgaga cttgcctttt     1500
ctctgcacgc aaagaagaac ttgtagggat caatcccgta actgatggta ctacccagaa    1560
atgggaccca atgaaagacc attggcggtt ctgttcggtt ccaaagccga agaataatt      1620 gataaacaac attgagcaag attgccgtca gcaccgcaac ggccatgtag gccgtaagcc     1680
atagcatcgg caccatttcg aggagacaca gggagggtga gcccgaggat tagagttgca     1740
gtgatgaggg aaatgaaaaa gaataggagg aaaatggata agagggatta tttcatatac     1800
tggattcctt aaggcctagg acaaggacga atgagagacc agctaatgaa aaacatgttc     1860
catgctgtat tttatattca cctacctacc aatataggtt cataggtaag tagatctacc     1920
taccgtagta tgagttaggg tgtatggtat gctggaacta caccttagta attaggcaac     1980
tttcattcgg ctcagcacac atccggaccg cgtgattcta gacaactctg aagtggtgct     2040
gcgattat                                                              2048
```

<210> SEQ ID NO 16
<211> LENGTH: 24
<212> TYPE: DNA
<213> ORGANISM: Aspergillus fumigatus

<400> SEQUENCE: 16
tcattgggtc ccatttctgg gtag      24

<210> SEQ ID NO 17
<211> LENGTH: 24
<212> TYPE: DNA
<213> ORGANISM: Aspergillus fumigatus

<400> SEQUENCE: 17
tagacctctt ccgcattgac atcc      24

<210> SEQ ID NO 18
<211> LENGTH: 19
<212> TYPE: DNA
<213> ORGANISM: Aspergillus fumigatus

<400> SEQUENCE: 18
tctgggtagt accatcagt      19

<210> SEQ ID NO 19
<211> LENGTH: 19
<212> TYPE: DNA
<213> ORGANISM: Aspergillus fumigatus

<400> SEQUENCE: 19
tgggtagtac catcagtta      19

<210> SEQ ID NO 20
<211> LENGTH: 18
<212> TYPE: DNA
<213> ORGANISM: Aspergillus fumigatus

<400> SEQUENCE: 20
tgggtagtac catcagtt                                                 18

<210> SEQ ID NO 21
<211> LENGTH: 17
<212> TYPE: DNA
<213> ORGANISM: Aspergillus fumigatus

<400> SEQUENCE: 21
gtagtaccat cagttac                                                  17

<210> SEQ ID NO 22
<211> LENGTH: 19
<212> TYPE: DNA
<213> ORGANISM: Aspergillus fumigatus

<400> SEQUENCE: 22
gaagaacttg tagggatca                                                19

<210> SEQ ID NO 23
<211> LENGTH: 19
<212> TYPE: DNA
<213> ORGANISM: Aspergillus fumigatus

<400> SEQUENCE: 23
aagaacttgt agggatcaa                                                19

<210> SEQ ID NO 24
<211> LENGTH: 20
<212> TYPE: DNA
<213> ORGANISM: Aspergillus fumigatus

<400> SEQUENCE: 24
aagaagaact tgtagggatc                                               20

<210> SEQ ID NO 25
<211> LENGTH: 19
<212> TYPE: DNA
<213> ORGANISM: Aspergillus fumigatus

<400> SEQUENCE: 25
agaacttgta gggatcaat                                                19

<210> SEQ ID NO 26
<211> LENGTH: 25
<212> TYPE: DNA
<213> ORGANISM: Aspergillus fumigatus

<400> SEQUENCE: 26
aaaccacagt ctacctgggc gttca                                         25

<210> SEQ ID NO 27
<211> LENGTH: 25
<212> TYPE: DNA
<213> ORGANISM: Aspergillus fumigatus

<400> SEQUENCE: 27

```
tgaacgccca ggtagactgt ggttt                                        25

<210> SEQ ID NO 28
<211> LENGTH: 24
<212> TYPE: DNA
<213> ORGANISM: Aspergillus fumigatus

<400> SEQUENCE: 28
atgtcaatgc ggaagaggtc tata                                         24

<210> SEQ ID NO 29
<211> LENGTH: 21
<212> TYPE: DNA
<213> ORGANISM: Aspergillus fumigatus

<400> SEQUENCE: 29
tcggacgtgg tgtatgattg t                                            21

<210> SEQ ID NO 30
<211> LENGTH: 21
<212> TYPE: DNA
<213> ORGANISM: Aspergillus fumigatus

<400> SEQUENCE: 30
ccttgaaagt tcggtgaatc g                                            21

<210> SEQ ID NO 31
<211> LENGTH: 20
<212> TYPE: DNA
<213> ORGANISM: Aspergillus fumigatus

<400> SEQUENCE: 31
cagaaaaagt tcatcaagta                                              20

<210> SEQ ID NO 32
<211> LENGTH: 17
<212> TYPE: DNA
<213> ORGANISM: Aspergillus fumigatus

<400> SEQUENCE: 32
aacgcagact gagtcaa                                                 17

<210> SEQ ID NO 33
<211> LENGTH: 32
<212> TYPE: DNA
<213> ORGANISM: Aspergillus fumigatus

<400> SEQUENCE: 33
gtctgcgtta gagtctcatg tgccacttat tg                                32

<210> SEQ ID NO 34
<211> LENGTH: 32
<212> TYPE: DNA
<213> ORGANISM: Aspergillus fumigatus

<400> SEQUENCE: 34
caataagtgg cacatgagac tctaacgcag ac                                32

<210> SEQ ID NO 35
<211> LENGTH: 23
<212> TYPE: DNA
<213> ORGANISM: Aspergillus fumigatus

<400> SEQUENCE: 35
```
ttaccatttt taccgctgct cga                                          23

<210> SEQ ID NO 36
<211> LENGTH: 20
<212> TYPE: DNA
<213> ORGANISM: Aspergillus fumigatus

<400> SEQUENCE: 36
tgacctggac aagggcttta                                              20

<210> SEQ ID NO 37
<211> LENGTH: 24
<212> TYPE: DNA
<213> ORGANISM: Aspergillus fumigatus

<400> SEQUENCE: 37
gtgcagttca tcaggttcca tatc                                         24

<210> SEQ ID NO 38
<211> LENGTH: 23
<212> TYPE: DNA
<213> ORGANISM: Aspergillus fumigatus

<400> SEQUENCE: 38
gagcagcatc tcgcttcttg tta                                          23

<210> SEQ ID NO 39
<211> LENGTH: 18
<212> TYPE: DNA
<213> ORGANISM: Aspergillus fumigatus

<400> SEQUENCE: 39
ggctttactc ccatcaat                                                18

<210> SEQ ID NO 40
<211> LENGTH: 15
<212> TYPE: DNA
<213> ORGANISM: Aspergillus fumigatus

<400> SEQUENCE: 40
atggggccca cggta                                                   15

<210> SEQ ID NO 41
<211> LENGTH: 26
<212> TYPE: DNA
<213> ORGANISM: Aspergillus fumigatus
<220> FEATURE:
<221> NAME/KEY: misc_feature
<222> LOCATION: (12)..(14)
<223> OTHER INFORMATION: n is a, c, g, or t

<400> SEQUENCE: 41
ccatcaattt tnnnctaccg tgggcc                                       26

<210> SEQ ID NO 42
<211> LENGTH: 26
<212> TYPE: DNA
<213> ORGANISM: Aspergillus fumigatus
<220> FEATURE:
<221> NAME/KEY: misc_feature
<222> LOCATION: (13)..(15)
<223> OTHER INFORMATION: n is a, c, g, or t

<400> SEQUENCE: 42

```
ggcccacggt agnnnaaaat tgatgg                                        26

<210> SEQ ID NO 43
<211> LENGTH: 23
<212> TYPE: DNA
<213> ORGANISM: Aspergillus fumigatus

<400> SEQUENCE: 43
caggctacta aggagcagga gaa                                          23

<210> SEQ ID NO 44
<211> LENGTH: 21
<212> TYPE: DNA
<213> ORGANISM: Aspergillus fumigatus

<400> SEQUENCE: 44
aagcgaattt ctcgccgata c                                            21

<210> SEQ ID NO 45
<211> LENGTH: 19
<212> TYPE: DNA
<213> ORGANISM: Aspergillus fumigatus

<400> SEQUENCE: 45
agcgaatttc tcgccgata                                               19

<210> SEQ ID NO 46
<211> LENGTH: 17
<212> TYPE: DNA
<213> ORGANISM: Aspergillus fumigatus

<400> SEQUENCE: 46
caagtcccta tcttccg                                                 17

<210> SEQ ID NO 47
<211> LENGTH: 15
<212> TYPE: DNA
<213> ORGANISM: Aspergillus fumigatus

<400> SEQUENCE: 47
agcggtgtcg gccag                                                   15

<210> SEQ ID NO 48
<211> LENGTH: 22
<212> TYPE: DNA
<213> ORGANISM: Aspergillus fumigatus
<220> FEATURE:
<221> NAME/KEY: misc_feature
<222> LOCATION: (12)..(14)
<223> OTHER INFORMATION: n is a, c, g, or t

<400> SEQUENCE: 48
atcttccgtt tnnngctggc cg                                           22

<210> SEQ ID NO 49
<211> LENGTH: 22
<212> TYPE: DNA
<213> ORGANISM: Aspergillus fumigatus
<220> FEATURE:
<221> NAME/KEY: misc_feature
<222> LOCATION: (9)..(11)
<223> OTHER INFORMATION: n is a, c, g, or t

<400> SEQUENCE: 49
cggccagcnn naaacggaag at                                           22
```

```
<210> SEQ ID NO 50
<211> LENGTH: 26
<212> TYPE: DNA
<213> ORGANISM: Aspergillus fumigatus

<400> SEQUENCE: 50
tacgggattg atccctacaa gttctt                                          26

<210> SEQ ID NO 51
<211> LENGTH: 15
<212> TYPE: DNA
<213> ORGANISM: Aspergillus fumigatus

<400> SEQUENCE: 51
tacgggattg atccc                                                      15
```